US008268786B2

(12) United States Patent
Sylvester et al.

(10) Patent No.: US 8,268,786 B2
(45) Date of Patent: Sep. 18, 2012

(54) ANTI-CANCER TOCOTRIENOL ANALOGUES AND ASSOCIATED METHODS

(75) Inventors: Paul W. Sylvester, West Monroe, LA (US); Khalid A. El Sayed, West Monroe, LA (US)

(73) Assignee: First Tech International Limited, Wanchai, Hong Kong (CN)

( * ) Notice: Subject to any disclaimer, the term of this patent is extended or adjusted under 35 U.S.C. 154(b) by 0 days.

(21) Appl. No.: 12/766,047

(22) Filed: Apr. 23, 2010

(65) Prior Publication Data

US 2010/0273869 A1    Oct. 28, 2010

Related U.S. Application Data

(60) Provisional application No. 61/172,035, filed on Apr. 23, 2009.

(51) Int. Cl.
*A01N 43/16* (2006.01)
*A61K 31/355* (2006.01)
*A61K 38/00* (2006.01)
*A61P 35/00* (2006.01)

(52) U.S. Cl. ...................................... 514/19.3; 514/458

(58) Field of Classification Search ......................... None
See application file for complete search history.

(56) References Cited

U.S. PATENT DOCUMENTS

| 6,043,269 | A  | 3/2000 | Jacobsen et al. |
| 6,387,882 | B1 | 5/2002 | Ogata |
| 6,441,029 | B1 | 8/2002 | Elson |
| 2007/0207196 | A1 | 9/2007 | Zhang |

FOREIGN PATENT DOCUMENTS

| WO | WO03/039461 A1 | 5/2003 |
| WO | WO2006094791 A1 | 9/2006 |

OTHER PUBLICATIONS

Golub e tal. Molecular Classification of Cancer: Class Discovery and Class Prediction by Gene Expression Monitoring, Science, 286, 531, 1999.*
Lala et al. Role of nitric oxide in tumor progression: Lessons from experimental tumors, Cancer and Metastasis Reviews, 17: 91-106, 1998.*
Hazem, et al., "Preparation and In Vitro Antiproliferative Effect of the Tocotrienol Loaded Lipid Nanoparticles Colloids and Surfaces," Oct. 30, 2009, pp. 43-51, Elsevier.
PCT search report and written opinion from PCT application No. PCT/US10/47454, Oct. 20, 2010.
PCT search report and written opinion from PCT application No. PCT/US11/23748, Jun. 9, 2011.
Shirode et. al., Synergistic anticancer effects of combined g-tocotrienol and celecoxib treatment are associated with suppression in Akt and NFkB signaling Biomedicine & Pharmacotherapy, Nov. 14, 2009, pp. 327-332, vol. 64, Elsevier.
Shirode et. al., Mechanisms Mediating the Synergistic Anticancer Effects of Combined γ-Tocotrienol and Celecoxib Treatment J. Bioanalysis & Biomedicine 2011, pp. 7-Jan., vol. 3(1).
Pearce et al., Inhibitors of Cholesterol Biosynthesis Hypocholesterolemic and Antioxidant Activities of Benzopyran and Tetrahydronaphthalene Analogues of the Tocotrienols Journal of Medicinal Chemistry, 1994, pp. 526-541, vol. 37, No. 4, American Chemical Society.
McIntyre et al. Antiproliferative and Apoptotic Effects of Tocopherols and Tocotrienols on Preneoplastic and Neoplastic Mouse Mammary Epithelial Cells Society for Experimental Biology and Medicine, 2000, pp. 292-301, vol. 224.
Sylvester et al., Role of Tocotrienols in the Prevention of Cardiovascular Disease and Breast Cancer Current Topics in Nutraceutical Research, 2003, pp. 1-16 vol. 1(2).
Shah et al., Tocotrienol-Induced Caspase-8 Activation Is Not Associated with Death Receptor Apoptotic Signaling in Neoplastic Mammary Epithelial Cells Society for Experimental Biology and Medicine, 2004 p. 229.
Shah et al., γ-Tocotrienol Inhibits Neoplastic Mammary Epithelial Cell Proliferation by Decreasing Akt and Nuclear Factor κb, Activity Society for Experimental Biology and Medicine, 2005, pp. 235-241.
Shah et al., Tocotrienol-induced cytotoxicity is unrelated to mitochondrial stress apoptotic signaling in neoplastic mammary epithelial cells, Biochem. Cell Biol., 2005, pp. 86-95, vol. 83.
Matter et al., Structural Requirements for Factor Xa Inhibition by 3-Oxybenzamides with Neutral P1 Substituents: Combining X-ray Crystallography, 3D-QSAR and Tailored Scoring Functions, Journal of Medical Chemistry, Apr. 13, 2005, pp. 3290-3312, vol. 25 American Chemical Society.
Samant et al., γ-Tocotrienol inhibits ErbB3-dependent PI3K/Akt mitogenic signalling in neoplastic mammary epithelial cells Cell Proliferation, 2006, pp. 563-574, vol. 39, Blackwell Publishing Ltd.
Sylvester, Vitamin E and Apoptosis Vitamins and Hormones, 2007, pp. 329-356, vol. 76, Elsevier, Inc.
Kashiwagi et al., A redox-silent analogue of tocotrienol inhibits hypoxic adaption of lung cancer cells, Biochemical and Biophysical Research Communication, Nov. 8, 2007, pp. 875-881, vol. 365, Elsevier, Inc.
Constantinou et al., Vitamin E and cancer: an insight into the anticancer activities of vitamin E isomers and analogs, International Journal of Cancer, May 29, 2008, pp. 739-752, vol. 123, Wiley-Liss, Inc.
Chang et al., Evidence of γ-Tocotrienol as an Apoptosis-Inducing, Invastion-Suppressing, and Chemotherapy Drug-Sensitizing Agent in Human Melanoma Cells Nutrition and Cancer, Nutrition and Cancer, 2009, pp. 357-366, vol. 61 (3).
Wali et al., Combined Treatment of c-Tocotrienol with Statins Induce Mammary Tumor Cell Cycle Arrest in G1, Society for Experimental Biology and Medicine, 2009, pp. 639-650.

(Continued)

*Primary Examiner* — Brandon Fetterolf
*Assistant Examiner* — Anna Pagonakis
(74) *Attorney, Agent, or Firm* — Edel Patents LLC; John B. Edel

(57) ABSTRACT

Compounds are disclosed relating to the treatment of cancer that include tocotrienols and derivatives of tocotrienols including 2,5,7,8-tetramethyl-2-((3E,7E)-4,8,12-trimethyltrideca-3,7,11-trienyl)chroman-6-ylphenylsulfonylcarbamate; (R)-2,8-dimethyl-2-((3E,7E)-4,8,12-trimethyltrideca-3,7,11-trienyl)chroman-6-yl tosylcarbamate; and (R)-2,5,7,8-tetramethyl-2-((3E,7E)-4,8,12-trimethyltrideca-3,7,11-trienyl)chroman-6-yl benzylcarbamate. Therapeutic uses of these types of compounds are also taught.

120 Claims, 6 Drawing Sheets

OTHER PUBLICATIONS

Ali et al., Development and validation of a reversed-phase HPLC method for the simultaneous analysis of simvastatin and tocotrienols in combined dosage forms, Journal of Pharmaceutical and Biomedical Analysis, Feb. 20, 2009, pp. 950-956, vol. 49 2009, Elsevier, Inc.
Wali et al., Endoplasmic reticulum stress mediates c-tocotrienol-induced apoptosis in mammary tumor cells, Apoptosis, Sep. 23, 2009, pp. 1366-1377, vol. 14.
Elnagar et al., Design and preliminary structure—activity relationship of redox-silent semisynthetic tocotrienol analogues as inhibitors for breast cancer proliferation and invasion, Bioorganic & Medicinal Chemistry, Nov. 27, 2009, pp. 755-768, vol. 18, Elsevier, Inc.
Gupte et al., CoMFA and CoMSIA 3D-QSAR Studies on S6-(4-nitrobenzyl)mercaptopurine riboside (NBMPR) analogs as inhibitors of human equilibrative nucleoside transporter 1 (Hent1), Bioorganic & Medicinal Chemistry Letters, 2009, pp. 314-318, vol. 19, Elsevier, Inc.
Abuasal et al., Intestinal Absorption of γ-Tocotrienol Is Mediated by Niemann-Pick C1-Like 1: In Situ Rat Intestinal Perfusion Studies, Drug Metabolism and Disposition, 2010, pp. 939-945, vol. 38(6).
Aggarwal et al., Tocotrienols, the vitamin E of the 21st century: Its potential against cancer and other chronic diseases, Biochemical Pharmacology, 2010, pp. 1-19, vol. 10676, Elsevier, Inc.
Bachawal et al., Enhanced antiproliferative and apoptotic response to combined treatment of g-tocotrienol with erlotinib or gefitinib in mammary tumor cells, BMC Cancer, 2010, pp. 1-13, vol. 10:14.
Bachawal et al., Combined γ-Tocotrienol and Erlotinib/Gefitinib Treatment Suppresses Stat and Akt Signaling in Murine Mammary Tumor Cells, Anticancer Research, 2010, pp. 429-438, vol. 30.
Mudit Synthesis of Fluorescent Analogues of the Anticancer Natural Products 4-Hydroxyphenylmethylene Hydantoin and δ-Tocotrienol, Natural Product Communications, 2010, pp. 1623-1626, vol. 5(10), Natural Product Communications, Westerville, Ohio.
Samant et al., Anti-proliferative effects of c-tocotrienol on mammary tumour cells are associated with suppression of cell cycle progression, Cell Proliferation, 2010, pp. 77-83, vol. 43, Blackwell Publishing Ltd.
Sylvester et al., The Value of Tocotrienols in the Prevention and Treatment of Cancer, Journal of the American College of Nutrition, 2010, pp. 324S-333S, vol. 29(3), American College of Nutrition.
El Sayed et al., Biocatalytic and semisynthetic optimization of the anti-invasive tobacco (1S,2E,4R,6R,7E,11E)-2,7,11-cembratriene-4,6-diol, Bioorganic & Medicinal Chemistry, Jan. 3, 2008, pp. 8066-8075, vol. 18, Elsevier, Inc.
Ali et al., Preparation, characterization, and anticancer effects of simvastatin—tocotrienol lipid nanoparticles, International Journal of Pharmaceutics, Feb. 10, 2010, pp. 233-231, vol. 389, Elsevier, Inc.
Ali et al., Molecular interaction and localization of tocotrienol-rich fraction (TRF) within the matrices of lipid nanoparticles: Evidence studies by Differential Scanning Calorimetry (DSC) and Proton Nuclear Magnetic Resonance spectroscopy (1H NMR) Colloids and Surfaces B:, Biointerfaces, 2010, pp. 286-297, vol. 77, Elsevier, Inc.
Behery et al., Redox-silent tocotrienol esters as breast cancer proliferation and migration inhibitors, Bioorganic & Medicinal Chemistry, 2010, pp. 8069-8075, vol. 18, Elsevier, Inc.
Ali et al., Preparation, characterization, and anticancer effects of simvastatin—tocotrienol lipid nanoparticles Colloids and Surfaces A: Physiochem. Eng., Aspects, Oct. 30, 2009, pp. 43-51, vol. 353, Elsevier, Inc.

ACS SciFinder search engine results, http://www.cas.org/products/sfacad/index.html Query: Tocotrienol.
ACS SciFinder search engine results, http://www.cas.org/products/sfacad/index.html Query: Bioavailability Tocotrienol.
ACS SciFinder search engine results, http://www.cas.org/products/sfacad/index.html Query: Tocotrienol Potential Anticancer.
ACS SciFinder search engine results, http://www.cas.org/products/sfacad/index.html Query: Solubility Tocotrienol.
ACS SciFinder search engine results, http://www.cas.org/products/sfacad/index.html Query: Structure Search 1.
ACS SciFinder search engine results, http://www.cas.org/products/sfacad/index.html Query: Structure Search 3.
ACS SciFinder search engine results, http://www.cas.org/products/sfacad/index.html Query: Structure Search 2.
PCT search report and written opinion from PCT application No. PCT/US 10/32262.
Sen, et al., Journal of Biol Chem, 2000, pp. 13049, vol. 275.
Crowell, et al., Journal Biol Chem, 1991, pp. 17679, vol. 266.
Elson, et al., Journal Nutr., 1994, pp. 607, vol. 124.
Sporn, et al., Nat. Rev. Cancer, 2002, pp. 537, vol. 2.
Shukla, et al., Nutr. Cancer, 2005, pp. 18, vol. 53.
Nesaretnam, et al., Lipids, 1995, pp. 1139, vol. 30.
Qureshi, et al., Atherosclerosis, 2002, pp. 199, vol. 161.
Khanna, et al., Journal of Biol Chem, 2003, pp. 43508, vol. 278.
Akaho, et al., Drug Metab. Dispos., 2007, pp. 1502, vol. 35.
Takata, et al., Journal Lipid Res, 2002, pp. 2196, vol. 43.
Mazzini, et al., Journal Org. Chem, 2009, pp. 2063, vol. 13.
Tomic- Vatic, et. al., Int. J. Cancer, 2005, pp. 188, vol. 117.
Kashiwagi, et al., Biochem, Biophys. Res. Commun., 2008, pp. 875, vol. 365.
Ali, et al., Pharm Biomed. Anal., 2009, pp. 950, vol. 49.
Chang, et al., Nutr. Cancer, 2009, pp. 357, vol. 61.
Yap, et al., Br. J. Cancer, 2008, pp. 1832, vol. 99.
Tamilarasan, et al., Cell Biol., 2006, pp. 17, vol. 7.
Borghesani,, et al., Development, 2002, pp. 1435, vol. 6.
Kubinyi, et al., Burger's Medicinal Chemistry, 1995, pp. 497-571, vol. 1.
Denizot, et al., Immunol, Methods, 1986, pp. 271, vol. 89.
Kleinman, et al., Cancer Biol., 2005, pp. 378, vol. 15.
Koblinski, et al., Cancer Res., 2005, pp. 7370, vol. 65.
El Sayed et al., Latrunculin A and Its C-17-0 Carbamates Inhibit Prostate Tumor Cell Invasion and HIF-1 Activation in Breast Tumor Cells, Journal of Natural Products, 2008, pp. 396-402, vol. 71.
Arya et al., Design and synthesis of analogs of Vitamin E: Antiproliferative activity against human breast adenocarcinoma cells, Bioorganic Medicinal Chemistry Letters, Sep. 22, 1998, pp. 2433-2438, vol. 8(18).
McIntyre et al., Antiproliferative and Apoptotic Effects of Tocopherols and Tocotrienols on Normal Mouse and Mammary Epithelial Cells Lipids, 2000, pp. 171-180, vol. 35(2), AOCS Press.
Shah et al., Role of Caspase-8 Activation in Mediating Vitamin E-Induced Apoptosis in Murine Mammary Cancer Cells, Nutrition and Cancer, 2003, pp. 236-246, vol. 45(2), Lawrence Erlbaum Associates, Inc.
Liua et al., Inhibitory Effects of γ-tocotrienol on invastion and metastasis of human gastric denocarcinoma SGC-7901 Cells, Journal of Nutritional Biology, Feb. 5, 2009, vol. 11, Elsevier, Inc.

* cited by examiner

ANTI-CANCER TOCOTRIENOL ANALOGUES AND ASSOCIATED METHODS

This application claims the benefit of U.S. provisional patent application No. 61/172,035 filed Apr. 23, 2009 and entitled "Anti-Cancer Tocotrienol Analogues and Associated Methods."

The activity of known Vitamin E compounds is reduced due to poor absorption by the body and a short elimination half life in vivo. Therefore, there is a need for compounds related to known Vitamin E compounds that demonstrate features including: increased chemical and metabolic stability; increased water solubility; enhanced binding affinity for alpha-TT, caspase-3 and epidermal growth factor receptor (EGFR); increased antiangiogenic potency and/or increased antiproliferative effect.

Disclosed herein are embodiments of the present invention including compounds with anti-cancer effects, methods of making such compounds, and methods of cancer treatment and prevention involving those compounds that are useful in the fields of cancer treatment, prevention, and research. The compounds and methods of the present invention have the potential for development into lifesaving and/or life prolonging anti-cancer treatments. Further, the compounds and methods described herein are useful for the development of anti-cancer compounds and anti-cancer treatments in mammals and are useful as potent anti-oxidants. In particular, certain embodiments disclosed herein have demonstrated increased polarity, solubility in water, antiproliferative effects on cancer cells, cytotoxic effects on cancer cells, increased chemical stability, or combinations of these properties. Compounds disclosed herein may further show increased metabolic stability, improved distribution in the body, and enhanced binding affinity for caspase-3 and EGFR which may increase the anti-cancer effects of the compounds. Further, the compounds disclosed herein are useful as substitutes for known Vitamin E compounds. However, it is not necessary for each embodiment of the present invention to have all of the advantages disclosed above.

Several tocotrienols can be described by the following formula:

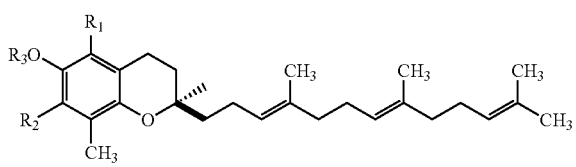

hereinafter referred to as General Formula 1.

α-tocotrienol, referred to herein as "Compound 1," is represented by General Formula 1 wherein $R_1$ is $CH_3$, and $R_2$ is $CH_3$, and $R_3$ is H.

β-tocotrienol is represented by General Formula 1 wherein $R_1$ is $CH_3$ and $R_2$ is H and $R_3$ is H.

γ-tocotrienol, referred to herein as "Compound 2," is represented by General Formula 1 wherein $R_1$ is H, $R_2$ is $CH_3$ and $R_3$ is H.

δ-tocotrienol, referred to herein as "Compound 3," is represented by General Formula 1 wherein $R_1$ is H, $R_2$ is H, and $R_3$ is H.

The Compounds 4-21 were synthesized from Compounds 1-3 as described below. These compounds were then tested for various activities pertinent to the treatment and/or prevention of cancer. Compounds 4-21 may be represented by General Formula I with additional reference to the functional groups listed below according to letter designations "a"-"f"

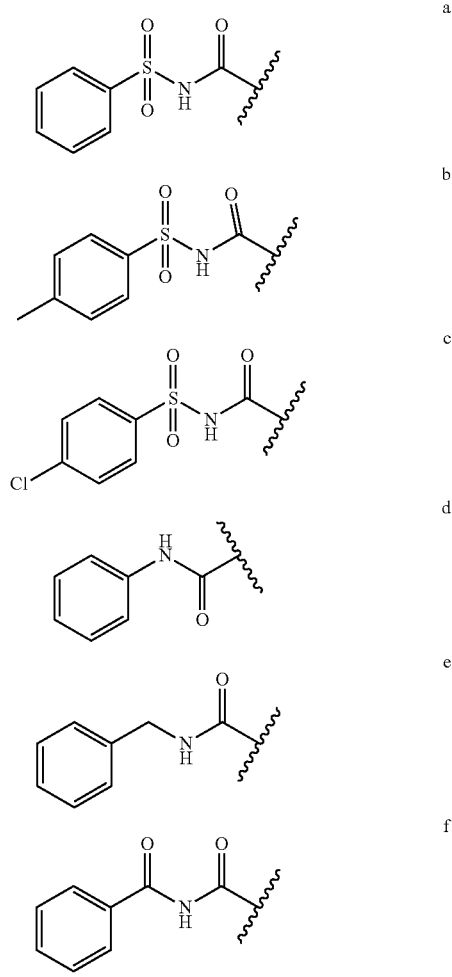

(referred to herein as Functional Group "a," Functional Group "b," etc.) and relate to individual embodiments of the invention and for that reason should not be construed to limit the scope of the invention either individually or as a group.

2,5,7,8-tetramethyl-2-((3E,7E)-4,8,12-trimethyltrideca-3,7,11-trienyl)chroman-6-ylphenylsulfonylcarbamate, referred to herein as "Compound 4," may be represented by General Formula 1 wherein $R_1$ is $CH_3$, $R_2$ is $CH_3$, and $R_3$ is Functional Group "a."

2,7,8-trimethyl-2-((3E,7E)-4,8,12-trimethyltrideca-3,7,11-trienyl)chroman-6-ylphenylsulfonylcarbamate, referred to herein as "Compound 5," may be represented by General Formula 1 wherein $R_1$ is H, $R_2$ is $CH_3$, and $R_3$ Functional Group "a."

2,8-dimethyl-2-((3E,7E)-4,8,12-trimethyltrideca-3,7,11-trienyl)chroman-6-ylphenylsulfonylcarbamate, referred to herein as "Compound 6," may be represented by General Formula 1 wherein $R_1$ is H, $R_2$ is H, and $R_3$ is Functional Group "a."

(R)-2,5,7,8-tetramethyl-2-((3E,7E)-4,8,12-trimethyl-trideca-3,7,11-trienyl)chroman-6-yl tosylcarbamate, referred to herein as "Compound 7," may be represented by General Formula 1 wherein $R_1$ is $CH_3$, $R_2$ is $CH_3$, and $R_3$ is Functional Group "b."

(R)-2,7,8-trimethyl-2-((3E,7E)-4,8,12-trimethyltrideca-3,7,11-trienyl)chroman-6-yl tosylcarbamate, referred to herein as "Compound 8," may be represented by General Formula 1 wherein $R_1$ is H, $R_2$ is $CH_3$, and $R_3$ is Functional Group "b."

(R)-2,8-dimethyl-2-((3E,7E)-4,8,12-trimethyltrideca-3,7,11-trienyl)chroman-6-yl tosylcarbamate, referred to herein as "Compound 9," may be represented by General Formula 1 wherein $R_1$ is H, $R_2$ is H, and $R_3$ is Functional Group "b."

(R)-2,5,7,8-tetramethyl-2-((3E,7E)-4,8,12-trimethyltrideca-3,7,11-trienyl)chroman-6-yl 4-chlorophenylsulfonylcarbamate, referred to herein as "Compound 10," may be represented by General Formula 1 wherein $R_1$ is $CH_3$, $R_2$ is $CH_3$, and $R_3$ is Functional Group "c."

(R)-2,7,8-trimethyl-2-((3E,7E)-4,8,12-trimethyltrideca-3,7,11-trienyl)chroman-6-yl 4-chlorophenylsulfonylcarbamate, referred to herein as "Compound 11," may be represented by General Formula 1 wherein $R_1$ is H, $R_2$ is $CH_3$, and $R_3$ is Functional Group "c."

(R)-2,8-dimethyl-2-((3E,7E)-4,8,12-trimethyltrideca-3,7,11-trienyl)chroman-6-yl 4-chlorophenylsulfonylcarbamate, referred to herein as "Compound 12," may be represented by General Formula 1 wherein $R_1$ is H, $R_2$ is H, and $R_3$ is Functional Group "c."

(R)-2,5,7,8-tetramethyl-2-((3E,7E)-4,8,12-trimethyltrideca-3,7,11-trienyl)chroman-6-yl phenylcarbamate, referred to herein as "Compound 13," may be represented by General Formula 1 wherein $R_1$ is $CH_3$, $R_2$ is $CH_3$, and $R_3$ is Functional Group "d."

(R)-2,7,8-trimethyl-2-((3E,7E)-4,8,12-trimethyltrideca-3,7,11-trienyl)chroman-6-yl phenylcarbamate, referred to herein as "Compound 14," may be represented by General Formula 1 wherein $R_1$ is H, $R_2$ is $CH_3$, $R_3$ is Functional Group "d."

(R)-2,8-dimethyl-2-((3E,7E)-4,8,12-trimethyltrideca-3,7,11-trienyl)chroman-6-yl phenylcarbamate, referred to herein as "Compound 15," may be represented by General Formula 1 wherein $R_1$ is H, $R_2$ is H, and $R_3$ is Functional Group "d."

(R)-2,5,7,8-tetramethyl-2-((3E,7E)-4,8,12-trimethyltrideca-3,7,11-trienyl)chroman-6-yl benzylcarbamate, referred to herein as "Compound 16," may be represented by General Formula 1 wherein $R_1$ is $CH_3$, $R_2$ is $CH_3$, and $R_3$ is Functional Group "e."

(R)-2,7,8-trimethyl-2-((3E,7E)-4,8,12-trimethyltrideca-3,7,11-trienyl)chroman-6-yl benzylcarbamate, referred to herein as "Compound 17," may be represented by General Formula 1 wherein $R_1$ is H, $R_2$ is $CH_3$, and $R_3$ is Functional Group "e."

(R)-2,8-dimethyl-2-((3E,7E) 4,8,12-trimethyltrideca-3,7,11-trienyl)chroman-6-yl benzylcarbamate, referred to herein as "Compound 18," may be represented by General Formula 1 wherein $R_1$ is H, $R_2$ is H, and $R_3$ is Functional Group "e."

(R)-2,5,7,8-tetramethyl-2-((3E,7E)-4,8,12-trimethyltrideca-3,7,11-trienyl)chroman-6-yl benzoylcarbamate, referred to herein as "Compound 19," may be represented by General Formula 1 wherein $R_1$ is $CH_3$, $R_2$ is $CH_3$, and $R_3$ is Functional Group "f."

(R)-2,7,8-trimethyl-2-((3E,7E)-4,8,12-trimethyltrideca-3,7,11-trienyl)chroman-6-yl benzoylcarbamate, referred to herein as "Compound 20," may be represented by General Formula I wherein $R_1$ is H, $R_2$ is $CH_3$, and $R_3$ is Functional Group "f."

(R)-2,8-dimethyl-2-((3E,7E)-4,8,12-trimethyltrideca-3,7,11-trienyl)chroman-6-yl benzoylcarbamate, referred to herein as "Compound 21," may be represented by General Formula 1 wherein $R_1$ is H, $R_2$ is H, and $R_3$ is Functional Group "f."

Compounds that may be represented by General Formula 1 wherein $R_1$ is $CH_3$, $R_2$ is H, and $R_3$ is a functional group selected Functional Groups "a," "b," "c," "d," "e," and "f" are referred to herein as the "Beta Tocotrienol Analogs."

The compositions disclosed herein may, for example, comprise a compound selected from: 2,5,7,8-tetramethyl-2-((3E,7E)-4,8,12-trimethyltrideca-3,7,11-trienyl)chroman-6-ylphenylsulfonylcarbamate; 2,7,8-trimethyl-2-((3E,7E)-4,8,12-trimethyltrideca-3,7,11-trienyl)chroman-6-ylphenylsulfonylcarbamate; 2,8-dimethyl-2-((3E,7E)-4,8,12-trimethyltrideca-3,7,11-trienyl)chroman-6-ylphenylsulfonylcarbamate; (R)-2,5,7,8-tetramethyl-2-((3E,7E)-4,8,12-trimethyltrideca-3,7,11-trienyl)chroman-6-yl tosylcarbamate; (R)-2,7,8-trimethyl-2-((3E,7E)-4,8,12-trimethyltrideca-3,7,11-trienyl)chroman-6-yl tosylcarbamate; (R)-2,8-dimethyl-2-((3E,7E)-4,8,12-trimethyltrideca-3,7,11-trienyl)chroman-6-yl tosylcarbamate; (R)-2,5,7,8-tetramethyl-2-((3E,7E)-4,8,12-trimethyltrideca-3,7,11-trienyl)chroman-6-yl 4-chlorophenylsulfonylcarbamate; (R)-2,7,8-trimethyl-2-((3E,7E)-4,8,12-trimethyltrideca-3,7,11-trienyl)chroman-6-yl 4-chlorophenylsulfonylcarbamate; (R)-2,8-dimethyl-2-((3E,7E)-4,8,12-trimethyltrideca-3,7,11-trienyl)chroman-6-yl 4-chlorophenylsulfonylcarbamate; (R)-2,5,7,8-tetramethyl-2-((3E,7E)-4,8,12-trimethyltrideca-3,7,11-trienyl)chroman-6-yl phenylcarbamate; (R)-2,7,8-trimethyl-2-((3E,7E)-4,8,12-trimethyltrideca-3,7,11-trienyl)chroman-6-yl phenylcarbamate; (R)-2,8-dimethyl-2-((3E,7E)-4,8,12-trimethyltrideca-3,7,11-trienyl)chroman-6-yl phenylcarbamate; (R)-2,5,7,8-tetramethyl-2-((3E,7E)-4,8,12-trimethyltrideca-3,7,11-trienyl)chroman-6-yl benzylcarbamate; (R)-2,7,8-trimethyl-2-((3E,7E)-4,8,12-trimethyltrideca-3,7,11-trienyl)chroman-6-yl benzylcarbamate; (R)-2,8-dimethyl-2-((3E,7E) 4,8,12-trimethyltrideca-3,7,11-trienyl)chroman-6-yl benzylcarbamate; (R)-2,5,7,8-tetramethyl-2-((3E,7E)-4,8,12-trimethyltrideca-3,7,11-trienyl)chroman-6-yl benzoylcarbamate; (R)-2,7,8-trimethyl-2-((3E,7E)-4,8,12-trimethyltrideca-3,7,11-trienyl)chroman-6-yl benzoylcarbamate; and (R)-2,8-dimethyl-2-((3E,7E)-4,8,12-trimethyltrideca-3,7,11-trienyl)chroman-6-yl benzoylcarbamate. Further compositions disclosed herein may comprise a pharmaceutically acceptable salt of one or more of these compounds or a combination of one or more of these salts and one or more of these compounds.

The compositions of matter disclosed herein may comprise a compound having the general structure of General Formula 1 wherein $R_1$ is either H or $CH_3$; wherein $R_2$ is either H or $CH_3$; and wherein $R_3$ is a functional group that causes the compound to classified as a carbamate.

In an embodiment based on the structure of General Formula 1, $R_3$ contains an aromatic ring. In another embodiment based on the structure of General Formula 1, the functional group $R_3$ is a group imparting greater water solubility to the compound than the water solubility of a natural tocotrienol having the same $R_1$ and $R_2$ groups. In another embodiment, the compound is a carbamate. In a further embodiment the compound is a tocotrienol-6-O-carbamate. In another embodiment, the compound has a polarity greater than or approximately equal to the polarity of γ-tocotrienol. In another embodiment, the polarity is less than or equal to the polarity of α-tocotrienol. In another embodiment, the compound has a molecular weight greater than or equal to 515.34. In another embodiment, the molecular weight is less than or equal to 621.35. In another embodiment, the functional group $R_3$ as shown in General Formula 1 contains a sulfur atom.

The compositions disclosed herein may, for example, comprise a first compound that is the product of one or more substitution reactions performed on a second compound, selected from α-tocotrienol, β-tocotrienol, γ-tocotrienol, and δ-tocotrienol; wherein the first compound has a feature selected from: anti-proliferative effects equivalent to or better than those of 2,8-dimethyl-2-((3E,7E)-4,8,12-trimethyltrideca-3,7,11-trienyl)chroman-6-ylphenylsulfonylcarbamate against human breast cancer cell line MCF7, anti-proliferative effects equivalent to or better than those of (R)-2,5,7, 8-tetramethyl-2-((3E,7E)-4,8,12-trimethyltrideca-3,7,11-trienyl)chroman-6-yl phenylcarbamate against human breast cancer cell line MDA-MB-231, and anti-invasive effects equivalent to or better than those of (R)-2,8-dimethyl-2-((3E,7E)-4,8,12-trimethyltrideca-3,7,11-trienyl)chroman-6-yl tosylcarbamate against human breast cancer cell line MDA-MB-231. In an additional embodiment a mammalian cell is exposed to that composition of matter thereby treating or preventing a form of cancer.

This disclosure teaches methods, for example, that may comprise administering to a mammalian patient in need of cancer treatment or prevention a composition selected from a first therapeutic amount of a compound and a second therapeutic amount of a pharmaceutically acceptable salt of the compound wherein the compound is selected from: 2,5,7,8-tetramethyl-2-((3E,7E)-4,8,12-trimethyltrideca-3,7,11-trienyl)chroman-6-ylphenylsulfonylcarbamate; 2,7,8-trimethyl-2-((3E,7E)-4,8,12-trimethyltrideca-3,7,11-trienyl)chroman-6-ylphenylsulfonylcarbamate; 2,8-dimethyl-2-((3E,7E)-4,8,12-trimethyltrideca-3,7,11-trienyl)chroman-6-ylphenylsulfonylcarbamate; (R)-2,5,7,8-tetramethyl-2-((3E,7E)-4,8,12-trimethyltrideca-3,7,11-trienyl)chroman-6-yl tosylcarbamate; (R)-2,7,8-trim ethyl-2-((3E,7E)-4,8,12-trimethyltrideca-3,7,11-trienyl)chroman-6-yl tosylcarbamate; (R)-2,8-dimethyl-2-((3E,7E)-4,8,12-trimethyltrideca-3,7,11-trienyl)chroman-6-yl tosylcarbamate; (R)-2,5,7,8-tetramethyl-2-((3E,7E)-4,8,12-trimethyltrideca-3,7,11-trienyl)chroman-6-yl 4-chlorophenylsulfonylcarbamate; (R)-2,7,8-trimethyl-2-((3E,7E)-4,8,12-trimethyltrideca-3,7,11-trienyl)chroman-6-yl 4-chlorophenylsulfonylcarbamate; (R)-2,8-dimethyl-2-((3E,7E)-4,8,12-trimethyltrideca-3,7,11-trienyl)chroman-6-yl 4-chlorophenylsulfonylcarbamate; (R)-2,5,7,8-tetramethyl-2-((3E,7E)-4,8,12-trimethyltrideca-3,7,11-trienyl)chroman-6-yl phenylcarbamate; (R)-2,7,8-trimethyl-2-((3E,7E)-4,8,12-trimethyltrideca-3,7,11-trienyl)chroman-6-yl phenylcarbamate; (R)-2,8-dimethyl-2-((3E,7E)-4,8,12-trimethyltrideca-3,7,11-trienyl)chroman-6-yl phenylcarbamate; (R)-2,5,7,8-tetramethyl-2-((3E,7E)-4,8,12-trimethyltrideca-3,7,11-trienyl)chroman-6-yl benzylcarbamate; (R)-2,7,8-trimethyl-2-((3E,7E)-4,8,12-trimethyltrideca-3,7,11-trienyl)chroman-6-yl benzylcarbamate; (R)-2,8-dimethyl-2-((3E,7E) 4,8,12-trimethyltrideca-3,7,11-trienyl)chroman-6-yl benzylcarbamate; (R)-2,5,7,8-tetramethyl-2-((3E,7E)-4,8,12-trimethyltrideca-3,7,11-trienyl)chroman-6-yl benzoylcarbamate; (R)-2,7,8-trimethyl-2-((3E,7E)-4,8,12-trimethyltrideca-3,7,11-trienyl)chroman-6-yl benzoylcarbamate; and (R)-2,8-dimethyl-2-((3E,7E)-4,8,12-trimethyltrideca-3,7,11-trienyl)chroman-6-yl benzoylcarbamate.

The methods disclosed herein may comprise exposing a mammalian cell to a composition selected from a first therapeutic amount of a compound and a second therapeutic amount of a pharmaceutically acceptable salt of the compound wherein the compound is selected from: 2,5,7,8-tetramethyl-2-((3E,7E)-4,8,12-trimethyltrideca-3,7,11-trienyl)chroman-6-ylphenylsulfonylcarbamate; 2,7,8-trimethyl-2-((3E,7E)-4,8,12-trimethyltrideca-3,7,11-trienyl)chroman-6-ylphenylsulfonylcarbamate; 2,8-dimethyl-2-((3E,7E)-4,8,12-trimethyltrideca-3,7,11-trienyl)chroman-6-ylphenylsulfonylcarbamate; (R)-2,5,7,8-tetramethyl-2-((3E,7E)-4,8,12-trimethyltrideca-3,7,11-trienyl)chroman-6-yl tosylcarbamate; (R)-2,7,8-trimethyl-2-((3E,7E)-4,8,12-trimethyltrideca-3,7,11-trienyl)chroman-6-yl tosylcarbamate; (R)-2,8-dimethyl-2-((3E,7E)-4,8,12-trimethyltrideca-3,7,11-trienyl)chroman-6-yl tosylcarbamate; (R)-2,5,7,8-tetramethyl-2-((3E,7E)-4,8,12-trimethyltrideca-3,7,11-trienyl)chroman-6-yl 4-chlorophenylsulfonylcarbamate; (R)-2,7,8-trimethyl-2-((3E,7E)-4,8,12-trimethyltrideca-3,7,11-trienyl)chroman-6-yl 4-chlorophenylsulfonylcarbamate; (R)-2,8-dimethyl-2-((3E,7E)-4,8,12-trimethyltrideca-3,7,11-trienyl)chroman-6-yl 4-chlorophenylsulfonylcarbamate; (R)-2,5,7,8-tetramethyl-2-((3E,7E)-4,8,12-trimethyltrideca-3,7,11-trienyl)chroman-6-yl phenylcarbamate; (R)-2,7,8-trimethyl-2-((3E,7E)-4,8,12-trimethyltrideca-3,7,11-trienyl)chroman-6-yl phenylcarbamate; (R)-2,8-dimethyl-2-((3E,7E)-4,8,12-trimethyltrideca-3,7,11-trienyl)chroman-6-yl phenylcarbamate; (R)-2,5,7,8-tetramethyl-2-((3E,7E)-4,8,12-trimethyltrideca-3,7,11-trienyl)chroman-6-yl benzylcarbamate; (R)-2,7,8-trimethyl-2-((3E,7E)-4,8,12-trimethyltrideca-3,7,11-trienyl)chroman-6-yl benzylcarbamate; (R)-2,8-dimethyl-2-((3E,7E) 4,8,12-trimethyltrideca-3,7,11-trienyl)chroman-6-ylbenzylcarbamate; (R)-2,5,7,8-tetramethyl-2-((3E,7E)-4,8,12-trimethyltrideca-3,7,11-trienyl)chroman-6-yl benzoylcarbamate; (R)-2,7,8-trimethyl-2-((3E,7E)-4,8,12-trimethyltrideca-3,7,11-trienyl)chroman-6-yl benzoylcarbamate; and (R)-2,8-dimethyl-2-((3E,7E)-4,8,12-trimethyltrideca-3,7,11-trienyl)chroman-6-yl benzoylcarbamate.

In another embodiment, the mammalian cell that is the subject of treatment or prevention is a cancerous cell. In another embodiment, the mammalian cell is a human cell. In another embodiment, the mammalian cell that is the subject of treatment or prevention is a breast cancer cell. In still another embodiment, the mammalian patient undergoing the method of treatment or prevention is a human.

In a prophetic embodiment, an in vivo product is produced by a process comprising administering one of the pharmacological compositions described herein to a mammalian patient by a form of delivery selected from: intravenous, intraperitoneal, subcutaneous, intramuscular, ocular, oral, transdermal, topical and inhalation wherein the in vivo product is present in a therapeutic amount.

In a prophetic embodiment, a method of treating a form of cancer comprises directing a human patient to internalize a composition of matter selected from a first therapeutic amount of a compound and a second therapeutic amount of a pharmaceutically acceptable salt of the compound, wherein the compound is one of the compounds disclosed herein and performing an assessment step selected from identifying the form of cancer, quantifying the form of cancer, and characterizing the form of cancer based on information from a test step selected from: a biopsy, an endoscopy, a bronchoscopy, a nasendoscopy; a X-ray, a CT scan, an MRI scan, an ultrasound, a scintigraphy, a single photon emission computed tomography, a positron emission tomography, and a blood test.

Several of the compositions disclosed herein may, for example, be represented by the following formula:

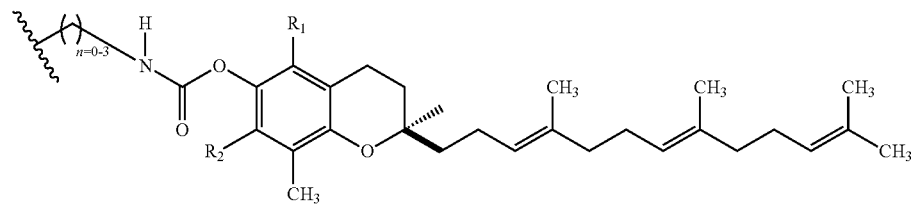

hereinafter referred to as General Formula 2 with additional reference to the functional groups listed below according to letter designations "g"-"n":

g 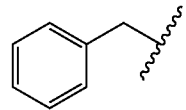

h 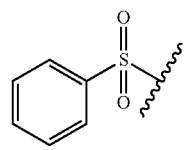

i 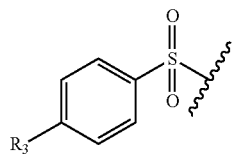

j 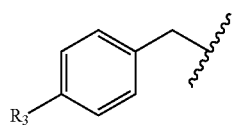

k 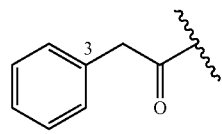

l 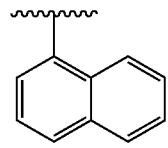

m 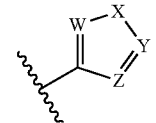

n 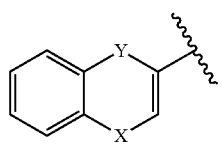

(referred to herein as Functional Group "g," Functional Group "h," etc.) and relate to individual prophetic embodiments of the invention.

Referring now to General Formula 2, for any of the functional groups that may be represented by functional groups "g"-"n" there is a compound set containing sixteen compounds that may be characterized by the members of Table 1. Each of the compounds taught with reference to Table 1 that do not represent compounds 4-21 should be considered a prophetic embodiment of the invention.

TABLE 1

| Compound Set Members | | | |
|---|---|---|---|
| Member 1 | $R_1 = CH_3$ | $R_2 = CH_3$ | $n = 0$ |
| Member 2 | $R_1 = H$ | $R_2 = CH_3$ | $n = 0$ |
| Member 3 | $R_1 = CH_3$ | $R_2 = H$ | $n = 0$ |
| Member 4 | $R_1 = H$ | $R_2 = H$ | $n = 0$ |
| Member 5 | $R_1 = CH_3$ | $R_2 = CH_3$ | $n = 1$ |
| Member 6 | $R_1 = H$ | $R_2 = CH_3$ | $n = 1$ |
| Member 7 | $R_1 = CH_3$ | $R_2 = H$ | $n = 1$ |
| Member 8 | $R_1 = H$ | $R_2 = H$ | $n = 1$ |
| Member 9 | $R_1 = CH_3$ | $R_2 = CH_3$ | $n = 2$ |
| Member 10 | $R_1 = H$ | $R_2 = CH_3$ | $n = 2$ |
| Member 11 | $R_1 = CH_3$ | $R_2 = H$ | $n = 2$ |
| Member 12 | $R_1 = H$ | $R_2 = H$ | $n = 2$ |
| Member 13 | $R_1 = CH_3$ | $R_2 = CH_3$ | $n = 3$ |
| Member 14 | $R_1 = H$ | $R_2 = CH_3$ | $n = 3$ |
| Member 15 | $R_1 = CH_3$ | $R_2 = H$ | $n = 3$ |
| Member 16 | $R_1 = H$ | $R_2 = H$ | $n = 3$ |

In an embodiment, compositions disclosed herein may comprise a compound selected from the Table 1 set members of the embodiment of General Formula 2 having functional group "g."

In a further embodiment, compositions taught herein may, for example, comprise a compound selected from the Table 1 set members of the embodiment of General Formula 2 having functional group "h."

In a further embodiment, compositions taught herein may, for example, comprise a compound selected from the Table 1 set members of the embodiment of General Formula 2 having functional group "i" wherein $R_3$ is $CH_3$.

In a further embodiment, compositions taught herein may, for example, comprise a compound selected from the Table 1 set members of the embodiment of General Formula 2 having functional group "i" wherein $R_3$ is $C_2H_5$.

In a further embodiment, compositions taught herein may, for example, comprise a compound selected from the Table 1 set members of the embodiment of General Formula 2 having functional group "i" wherein $R_3$ is isopropyl.

In a further embodiment, compositions taught herein may, for example, comprise a compound selected from the Table 1 set members of the embodiment of General Formula 2 having functional group "i" wherein $R_3$ is n-propyl.

In a further embodiment, compositions taught herein may, for example, comprise a compound selected from the Table 1 set members of the embodiment of General Formula 2 having functional group "i" wherein $R_3$ is n-butyl.

In a further embodiment, compositions taught herein may, for example, comprise a compound selected from the Table 1 set members of the embodiment of General Formula 2 having functional group "i" wherein $R_3$ is t-butyl.

In a further embodiment, compositions taught herein may, for example, comprise a compound selected from the Table 1 set members of the embodiment of General Formula 2 having functional group "i" wherein $R_3$ is isobutyl.

In a further embodiment, compositions taught herein may, for example, comprise a compound selected from the Table 1 set members of the embodiment of General Formula 2 having functional group "j" wherein $R_3$ is $CH_3$.

In a further embodiment, compositions taught herein may, for example, comprise a compound selected from the Table 1 set members of the embodiment of General Formula 2 having functional group "j" wherein $R_3$ is $C_2H_5$.

In a further embodiment, compositions taught herein may, for example, comprise a compound selected from the Table 1 set members of the embodiment of General Formula 2 having functional group "j" wherein $R_3$ is isopropyl.

In a further embodiment, compositions taught herein may, for example, comprise a compound selected from the Table 1 set members of the embodiment of General Formula 2 having functional group "j" wherein $R_3$ is n-propyl.

In a further embodiment, compositions taught herein may, for example, comprise a compound selected from the Table 1 set members of the embodiment of General Formula 2 having functional group "j" wherein $R_3$ is n-butyl.

In a further embodiment, compositions taught herein may, for example, comprise a compound selected from the Table 1 set members of the embodiment of General Formula 2 having functional group "j" wherein $R_3$ is t-butyl.

In a further embodiment, compositions taught herein may, for example, comprise a compound selected from the Table 1 set members of the embodiment of General Formula 2 having functional group "j" wherein $R_3$ is isobutyl.

In a further embodiment, compositions taught herein may, for example, comprise a compound selected from the Table 1 set members of the embodiment of General Formula 2 having functional group "k."

In a further embodiment, compositions taught herein may, for example, comprise a compound selected from the Table 1 set members of the embodiment of General Formula 2 having functional group "l."

In a further embodiment, compositions taught herein may, for example, comprise a compound selected from the Table 1 set members of the embodiment of General Formula 2 having functional group "m" wherein W is selected/from O, N, S, and C; wherein X is selected from O, N, S, and C; wherein Y is selected from O, N, S, and C; and wherein Z is selected from O, N, S, and C.

In a further embodiment, compositions taught herein may, for example, comprise a compound selected from the Table 1 set members of the embodiment of General Formula 2 having functional group "n" wherein Y is selected from O, N, S, and C; and wherein Z is selected from O, N, S, and C.

For each of the prophetic embodiments and the later disclosed prophetic examples, the preparation of compounds may be conducted based on a combination of the disclosures contained herein including reactions modeled on the examples and known compound preparation techniques.

Referring to the embodiments associated with General Formula 1 and General Formula 2 and the associated functional groups, compositions taught herein may, for example, have the oxygen adjacent to the ring structure associated with chromanol positioned between about 3 angstroms and about 6 angstroms from the center of the five or six member functional group ring center that is nearest the oxygen adjacent to the ring structure associated with chromanol. In a further embodiment, that distance is between about 4.5 angstroms and about 4.6 angstroms. In a further embodiment, that distance is between about 3 angstroms and about 4.6 angstroms. In a further embodiment, that distance is between about 4.5 angstroms and about 6 angstroms.

BRIEF DESCRIPTION OF THE DRAWINGS

FIG. 4A shows the MTT assay of the anti-invasive activities of the most active compounds, Compounds 1, 3, 9, 13, 16, and 17, against the ER-negative human breast cancer cells MDA-MB-231. The results show the percentage of invasion versus the μM concentrations of the compounds.

EXAMPLES

Examples 1-3

Figure 1:
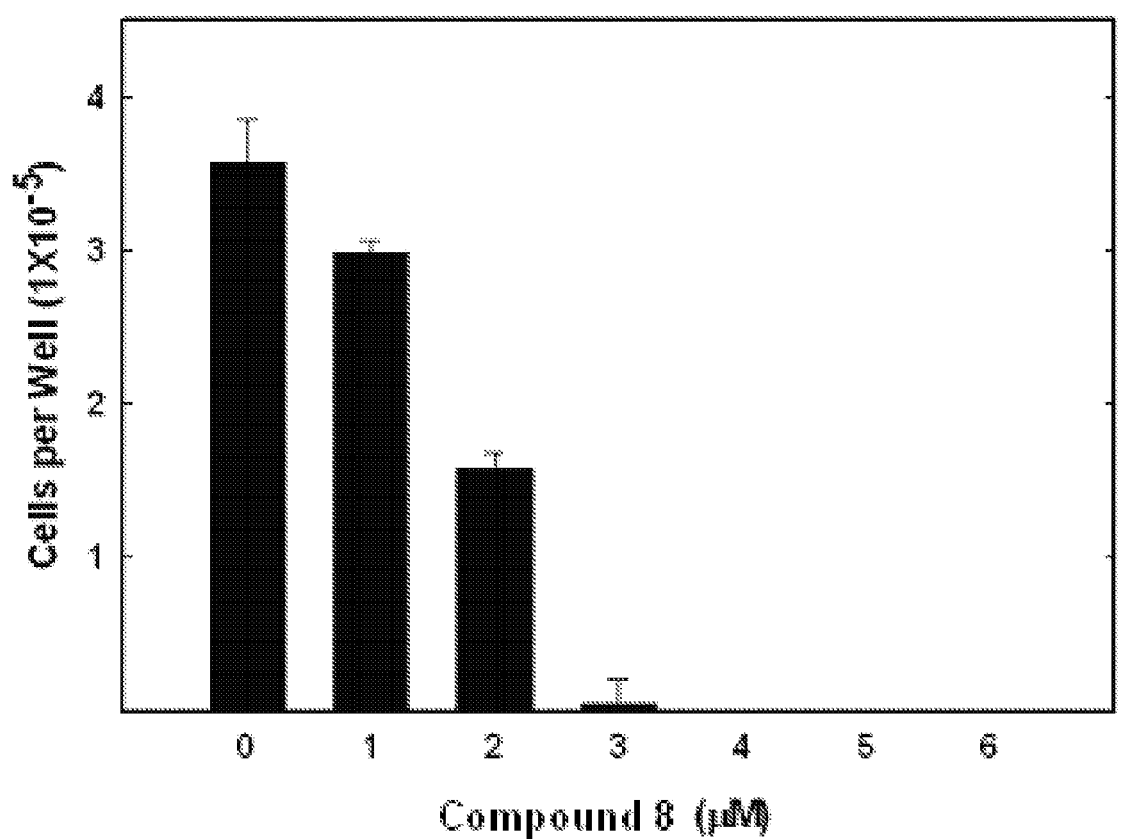
FIG. 1 shows the results from a MTT antiproliferative assay of Compound 8 against the highly malignant mouse+SA mammary epithelial cells.

Compounds 1-3 and beta-tocotrienol were prepared by purification using vacuum liquid chromatography (VLC) and high performance liquid chromatography (HPLC). Approximately 10 grams (g) of a tocotrienol-rich fraction of palm oil (TRF) was dissolved in 5 milliliters (mL) $CHCl_3$. Then approximately 10 g Diatomaceous Earth powder (Celite 545, E-Merck) was gradually added while mixing. The resulting semisolid paste was dried using a vacuum oven. After inserting a small piece of cotton at the bottom of a 2 Liter percolator the percolator was filled with 1 kilogram (Kg) silica gel 60 (230-400 mesh, Natland). The TRF-Diatomaceous Earth composition was then applied onto the top of the packed percolator and approximately 10 liters (L) of n-hexane-(99:1) or toluene-ethyl acetate (99:1) was used as a solvent system. 500-mL fractions were collected in 1 L Buchner flasks and elution was facilitated by applying a vacuum using the Buchner flask's side tube. The elution rate was approximately 3 mL per minute. α-Tocopherol was eluted first (approximately 2.5 g, 25% yield), followed by α-tocotrienol (approximately 2 g, 20% yield), γ-tocotrienol (approximately 3.5 g, 35% yield), O-tocotrienol (approximately 0.5 g, 5% yield) and δ-tocotrienol (approximately 1.5 g, 15% yield), respectively. Semi-preparative HPLC on Gimini 5μ C18 (Phenomenex), 75 cm×21.2 mm, 340 nm, UV detector, using isocratic 5 mL per min 5% water/methanol was used to purify mixtures of tocotrienols. Identification of purity was based on thin layer chromatography, $^1H$, and $^{13}C$ NMR analyses.

Tocotrienol analogs 4-21 were prepared by reaction of the purified natural tocotrienols Compounds 1-3 with corresponding isocyanates in toluene.

Example 4

Compound 4 was prepared by the following procedure. 6.30 microliters (mL) of benzene sufolnyl isocyanate was added to a solution comprising 20 mg of Compound 1 in 2 mL toluene. The resulting mixture was then gradually mixed with 10 μL of $Et_3N$. The reaction mixture was stirred at room temperature for 12 hours (h). 10 mL of water was then added, and the reaction mixture was extracted with three separate 10 mL extractions (EtOAc (3×10 mL)). The EtOAc extract was dried over anhydrous $Na_2SO_4$ and concentrated under reduced pressure. The crude product was then purified by column chromatography on silica gel 60 using methanol-n-hexane, 1:99, isocratic elution to yield Compound 4 (9 mg, 40%).

Example 5

Compound 5 was prepared by the following procedure. 32.63 mL of benzene sulfonyl isocyanate was added to a solution of 100 mg of Compound 2 in 2 mL toluene. The resulting mixture was gradually mixed with 10 µL of $Et_3N$. The reaction mixture was stirred at room temperature for 12 h. 10 mL of water was then added, and the product of the reaction mixture was extracted with EtOAc (3×10 mL). EtOAc extract was dried over anhydrous $Na_2SO_4$ and concentrated under reduced pressure. The dried crude mixture was then purified by column chromatography on silica gel 60 using methanol-$CHCl_3$, 1:99, isocratic elution, to yield Compound 5 (40 mg, 40%).

Example 6

Compound 6 was prepared by the following procedure. 11.70 mL of benzene sulfonyl isocyanate to solution of 50 mg of Compound 3 in 2 mL toluene. The resulting mixture was gradually mixed with 10 µL of $Et_3N$. The mixture was stirred at room temperature for 12 h. 10 mL of water (10 mL) was then added, and the product of the reaction mixture was extracted with EtOAc (3×10 mL). The EtOAc extract was dried over anhydrous $Na_2SO_4$ and concentrated under reduced pressure. The crude product was then purified by column chromatography on silica gel 60 using methanol-$CHCl_3$, 1:99, isocratic elution, to yield Compound 6 (20 mg, 40%).

Example 7

Compound 7 was prepared by the following procedure. 17.98 mL of p-toluenesulfonyl isocyante was added to a solution of 50 mg of Compound 1 in 2 mL toluene. The resulting mixture was gradually mixed with 10 µL of $Et_3N$. The mixture was stirred at room temperature for 12 h. 10 mL of water was then added, and the product of the reaction mixture was extracted with EtOAc (3×10 mL). The EtOAc extract was dried over anhydrous $Na_2SO_4$ and concentrated under reduced pressure. The dried crude mixture was then purified by column chromatography on silica gel 60 using methanol-$CHCl_3$, 1:99, to yield Compound 7 (25 mg, 50%).

Example 8

Compound 8 was prepared by the following procedure. 37.2 mL of p-toluenesulfonyl isocyaanate was added to a solution of 100 mg of Compound 2 in 2 mL toluene. The resulting mixture was mixed with 10 µL of $Et_3N$. The solution was stirred at room temperature for 12 h. 10 mL of water was then added, and the reaction mixture was extracted with EtOAc (3×10 mL). The EtOAc extract was dried over anhydrous $Na_2SO_4$ and concentrated under reduced pressure. The crude product was then purified by column chromatography on silica gel 60 using methanol, $CHCl_3$, 1:99, isocratic elution, to yield Compound 8 (60 mg, 60%).

Example 9

Compound 9 was prepared by the following procedure. 38.5 mL of p-toluenesulfonyl isocyanate was added to a solution of 100 mg of Compound 3 in 2 mL toluene. The resulting mixture was mixed with 10 µL of $Et_3N$. The mixture was stirred at room temperature for 12 h. 10 mL of water was then added, and the reaction mixture was extracted with EtOAc (3×10 mL). The EtOAc extract was dried over anhydrous $Na_2SO_4$ and concentrated under reduced pressure. The crude product was then purified by column chromatography on silica gel 60 using Methanol, $CHCl_3$, 1:99, isocratic elution, to yield Compound 9 (55 mg, 55%).

Example 10

Compound 10 was prepared by the following procedure. 35.17 mL of 4-chlorobenzene sulfonyl isocyanate was added to solution of 100 mg of Compound 1 in 2 mL toluene. The resulting mixture was gradually mixed with 10 µL of $Et_3N$. The solution was stirred at room temperature for 12 h. 10 mL of water was then added, and the reaction mixture was extracted with EtOAc (3×10 mL). The EtOAc extract was dried over anhydrous $Na_2SO_4$ and concentrated under reduced pressure. The crude product was then purified by column chromatography on silica gel 60 using Methanol, $CHCl_3$, 1:99, isocratic elution, to yield Compound 10 (45 mg, 45%).

Example 11

Compound 11 was prepared by the following procedure. 36.4 mL of 4-chlorobenzene sulfonyl isocyanate was added to a solution of 100 mg of Compound 2 in 2 mL toluene. The resulting mixture was mixed with 10 µL of $Et_3N$. The mixture was stirred at room temperature for 12 h. 10 mL of water was then added, and the reaction mixture was extracted with EtOAc (3×10 mL). The EtOAc extract was dried over anhydrous $Na_2SO_4$ and concentrated under reduced pressure. The crude product was then purified by column chromatography on silica gel 60 using methanol-$CHCl_3$, 1:99, isocratic elution, to yield Compound 11 (40 mg, 40%).

Example 12

Compound 12 was prepared by the following procedure. 37.60 of 4-chlorobenzene sulfonyl isocyanate was added to a solution of 100 mg of Compound 3 in 2 mL toluene. The resulting mixture was mixed with 10 µL of $Et_3N$. The solution was stirred at room temperature for 12 h. 10 mL of water was then added, and the reaction mixture was extracted with EtOAc (3×10 mL). The EtOAc extract was dried over anhydrous $Na_2SO_4$ and concentrated under reduced pressure. Crude product was then purified by column chromatography on silica gel 60 using methanol-$CHCl_3$, 1:99, isocratic elution to yield Compound 12 (50 mg, 50%).

Example 13

Compound 13 was prepared by the following procedure. 4.524 of phenyl isocyanate was added to a solution of 20 mg of Compound 1 in 2 mL toluene. The resulting mixture was then mixed with 10 µL of $Et_3N$. The mixture was stirred at room temperature for 3 h. 10 mL of water was then added, and the reaction mixture was extracted with EtOAc (3×10 mL). The EtOAc extract was dried over anhydrous $Na_2SO_4$ and concentrated under reduced pressure. The crude product was then purified by column chromatography on silica gel 60 using methanol-n-hexane, 1:99, isocratic elution to yield Compound 13 (10 mg, 50%).

Example 14

Compound 14 was prepared by the following procedure. 12.00 µL of phenyl isocyanate was added to a solution of 40 mg of Compound 2 in 2 mL toluene. The resulting mixture was mixed with 10 µL of Et₃N. The mixture was stirred at room temperature for 3 h. 10 mL of water was then added, and the reaction mixture was extracted with EtOAc (3×10 mL). The EtOAc extract was dried over anhydrous Na₂SO₄ and concentrated under reduced pressure. The crude product was then purified by column chromatography on silica gel 60 using methanol-CHCl₃, 1:99, isocratic elution, to yield Compound 14 (20 mg, 50%).

Example 15

Compound 15 was prepared by the following procedure. 27.40 µL of phenyl isocyanate was added to a solution of 100 mg of Compound 3 in 2 mL toluene. The resulting mixture was mixed with 10 µL of Et₃N. Solution was stirred at room temperature for 3 h. 10 mL of water was then added, and the reaction mixture was extracted with EtOAc (3×10 mL). The EtOAc extract was dried over anhydrous Na₂SO₄ and concentrated under reduced pressure. The crude product was then purified by column chromatography on silica gel 60 using methanol-CHCl₃, 1:99, to yield Compound 15 (50 mg, 50%).

Example 16

Compound 16 was prepared by the following procedure. 11.63 µl, of benzyl isocyanate was added to solution of 40 mg of Compound 1 in 2 mL toluene. The resulting mixture was mixed with 10 µL of Et₃N. The solution was stirred at room temperature for 3 h. 10 mL of water was then added, and the product of the reaction mixture was extracted with EtOAc (3×10 mL). The EtOAc extract was dried over anhydrous Na₂SO₄ and concentrated under reduced pressure. The crude product was then purified by column chromatography on silica gel 60 using methanol-n-hexane, 1:99, isocratic elution to yield Compound 16 (18 mg, 40%).

Example 17

Compound 17 was prepared by the following procedure. 16.31 µL of benzyl isocyanate was added to a solution of 50 mg of Compound 2 in 2 mL toluene. The resulting mixture was gradually mixed with 10 µL of Et₃N. The mixture was stirred at room temperature for 3 h. 10 mL of water was then added and the reaction mixture was extracted with EtOAc (3×10 mL). The EtOAc extract was dried over anhydrous Na₂SO₄ and concentrated under reduced pressure. The crude product was then purified by column chromatography on silica gel 60 using methanol-CHCl₃, 1:99, isocratic elution, to yield Compound 17 (20 mg, 40%).

Example 18

Compound 18 was prepared by the following procedure. 31.0 µL of benzyl isocyanate was added to a solution of 100 mg of Compound 3 in 2 mL toluene. The resulting mixture was added and gradually mixed with 10 µL of Et₃N. The mixture was stirred at room temperature for 3 h. 10 mL of water was then added and the reaction mixture was extracted with EtOAc (3×10 mL). The EtOAc extract was dried over anhydrous Na₂SO₄ and concentrated under reduced pressure. The crude product was then purified by column chromatography on silica gel 60 using methanol-CHCl₃, 1:99, to yield Compound 18 (40 mg, 40%).

Example 19

Compound 19 was prepared by the following procedure. 31.2 pt of phenyl isocyanatoformate was added to a solution of 100 mg of Compound 1 in 2 mL toluene. The resulting mixture was added and mixed with 10 µL of Et₃N. The solution was stirred at room temperature for 3 h. 10 mL of water was then added, and the product of the reaction mixture was extracted with EtOAc (3×10 mL). EtOAc extract was dried over anhydrous Na₂SO₄ and concentrated under reduced pressure. Crude product was then purified by column chromatography on silica gel 60 using methanol-CHCl₃, 1:99, isocratic elution to yield compound 19 (60 mg, 60%).

Example 20

Compound 20 was prepared by the following procedure. 32.2 µL of phenyl isocyanatoformate was added to a solution of 50 mg of Compound 2 in 2 mL toluene. The resulting mixture was gradually mixed with 10 µL of Et₃N. The mixture was stirred at room temperature for 3 h. 10 mL of water was then added and the reaction mixture was extracted with EtOAc (3×10 mL). The EtOAc extract was dried over anhydrous Na₂SO₄ and concentrated under reduced pressure. Crude product was then purified by column chromatography on silica gel 60 using methanol-CHCl₃, 1:99, isocratic elution, to yield compound 20 (70 mg, 70%).

Example 21

Compound 21 was prepared by the following procedure. 33.4 µL of phenyl isocyanatoformate was added to a solution of 100 mg of Compound 3 in 2 mL toluene. The resulting mixture was gradually mixed with 10 µL of Et₃N. The mixture was stirred at room temperature for 3 h. 10 mL of water was then added and the reaction mixture was extracted with EtOAc (3×10 mL). The EtOAc extract was dried over anhydrous Na₂SO₄ and concentrated under reduced pressure. The crude product was then purified by column chromatography on silica gel 60 using methanol-CHCl₃, 1:99; to yield compound 21 (65 mg, 65%).

Example 22

In a prophetic example, the Beta Tocotrienol Analogs are prepared utilizing the same methods as described in the preparation of Compounds 1-21 with the use of β-tocotrienol in the place of Compounds 1-3.

Example 23

The antiproliferative effects of Compounds 1-21 were tested using 3-(4,5-dimethylthiazol-2-yl)-2,5-diphenyl tetrasolium bromide (MTT) colorimetric assay utilizing cultures of the highly malignant+SA mouse mammary epithelial cell line maintained on serum-free media and containing 10 ng/mL epidermal growth factor (EGF) and 10 µg/mL insulin as mitogens using 24-well culture plates (6 wells/group) by MTT assay.

Cells were then divided into different treatment groups and given fresh control or treatment media every day. In growth inhibition studies, (IC50), +SA cells were treated with various doses of individual tocotrienol or tocotrienol derivatives for 4 days and then the viable cell number was determined using the MTT assay. Optical density of each sample was read at 570 nm on a microplate reader (SpectraCount, Packard BioScience Company, Meriden, Conn.) against a blank prepared from cell-free cultures. The number of cells/well was calculated against a standard curve prepared by plating various concentrations of cells, as determined by hemocytometer, at the start of each experiment. See McIntyre referenced above.

For each of the assays performed the compounds were dissolved in aqueous culture media by binding the compounds with bovine serum albumin (BSA).

An amount of each compound appropriate for the desired final compound concentration was placed in a 1.5 mL screw top glass vial and dissolved in 100 μL of 100% ethanol. Once dissolved, this ethanol/compound solution was added to a small volume of sterile 10% BSA in water and incubated overnight at 37° C. This solution of compound bound to BSA was then used to prepare various concentrations (0-1000 μM) of compound supplemented treatment media such that the control and treatment media had a final concentration of 5 mg/mL BSA. Ethanol was added to all treatment media such that the final ethanol concentration was the same in all treatment groups within a given experiment and was always less than 0.1%. Although the examples provided have been described in conjunction with specified amounts of ethanol and other compounds it should be understood that the invention is applicable to embodiments not having those limited concentration.

Compounds 4-21 showed antiproliferative activity against the highly malignant+SA mice mammary epithelial cells. Compound 8 was the most active with an $IC_{50}$ of 2.00 μM. Compound 8 was nearly 2-fold as active as its parent γ-tocotrienol (2) against this cell line (FIG. 1). The advantages of Compound 8 over Compound 2 include better chemical stability, which could impart better metabolic stability, increased polarity and therefore better water solubility, and it is expected that Compound 8 will have distribution and bioavailability better than that of Compound 2. Further, Compound 9 had activity better than that of its parent tocotrienol and Compounds 1-3, 5-7, and 10-21 each showed statistically significant anti-proliferative activity against this cell line. FIG. 1 shows assay results for Compound 8 against the highly malignant+SA mice mammary epithelial cells for various micro molar concentrations of that compound.

Example 24

The cell growth of MCF7 (Example 24) and MDA-MB-231 (Example 25) cell lines was measured using the MTT assay procedures described above and an MTT assay kit (TACS™, Trevogen®, Inc., Gaithersburg, Md.). After passing the cells for 3-4 times, growing cells were incubated in a 96-well plate at a density of 8×10³ cells per well, and allowed to attach for 24 hours. Complete growth medium was then replaced with 100 μL of RPMI serum free medium (GIBCO-Invitrogen, NY) containing various doses (20, 10, 5, 2 μM) of the tested compound and the culture continued at 37° C. under 5% $CO_2$. After 96 hours, the incubated cells were treated with MTT solution (10 μL/well) at 37° C. for 4 hours. The color reaction was stopped by the addition of solubilization/stop solution (100 μL/well). The cells continued to be incubated at 37° C. to completely dissolve the formazan product. Absorbance of the samples was determined at 570 nm with an ELISA plate reader (BioTek, VT). Absorbance readings were converted to estimated cell numbers based on a standard curve prepared by plating various concentration of cells, as determined by hemocytometer, and measuring the absorbance of those cells at the start of each experiment. The $IC_{50}$ value of each compound was calculated using nonlinear regression (curve fit) of log concentration versus the number of cells/well implemented using GraphPad Prism 5.0 program. The procedure was identical for both human breast cancer cell lines MCF7 and MDA-MB-231.

Figure 2:
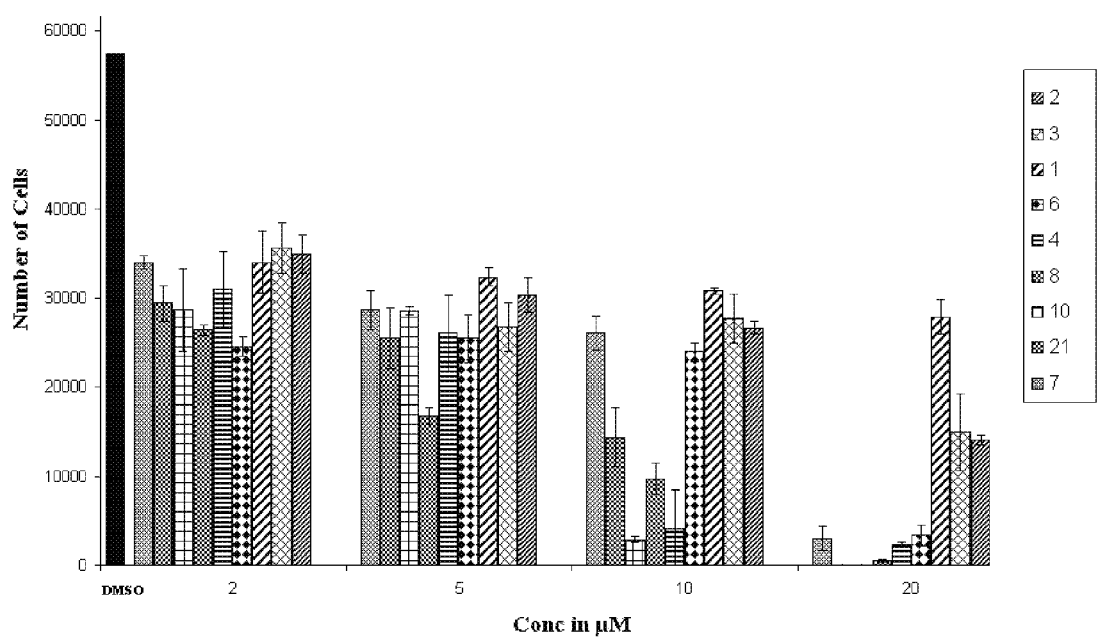
FIG. 2A shows the MTT antiproliferative assay of the most active compounds, Compounds 1-4, 6-8,10, and 21, against ER-positive MCF-7 human breast cancer cells. The results show the number of cells versus the μM concentrations of the compounds.
FIG. 2B shows the MTT antiproliferative assay of the most active compounds, Compounds 1-4, 6-8, 10, and 21, against ER-positive MCF-7 human breast cancer cells. The results show the percentage of cell growth versus the μM concentrations of the compounds.
Figure 2:
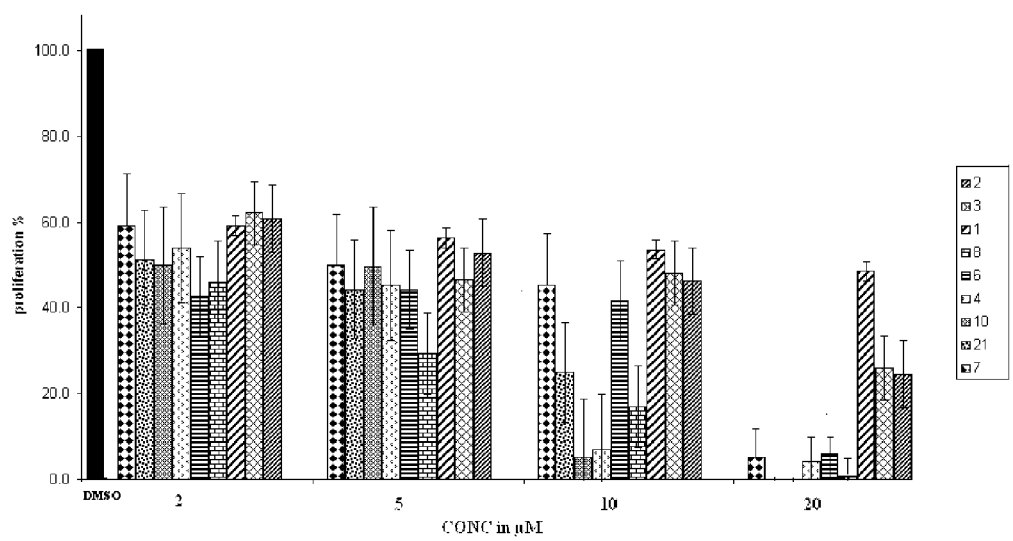

Compounds 4-18 and 21 showed antiproliferative activity against the ER-positive human breast cancer cells MCF7. Compounds 4, 6-8, 10, 21 showed improved activities versus the starting natural products 1-3 (FIG. 2). The most active compounds were 4, 8, and 10 with $IC_{50}$ values of 5-10 μM. Calculated $IC_{50}$ values are shown in Table 2 below. This is significant because compounds 4 and 10 are analogs of α-tocotrienol, which is the least active of the natural tocotrienols. The advantages of compounds 4 and 10 versus 1, in addition to 8-fold potency, include more chemical stability which could impart better metabolic stability, increased polarity, and therefore better water solubility. Additionally, it is expected that compounds 4 and 10 will have distribution and bioavailability better than that of Compound 1. Compounds 6 and 7 showed activities greater than the natural tocotrienols from which they were derived. Compounds 1-3, 5, 9, and 11-21 each showed statistically significant anti-proliferative activity. Compound 8 was nearly 3-fold as active as its parent γ-tocotrienol, Compound 2, against this cell line. FIGS. 2A and 2B show assay results for the most active of the compounds against the ER-positive human breast cancer cells MCF7 for various micro molar concentrations of the compounds.

Example 25

Figure 3:
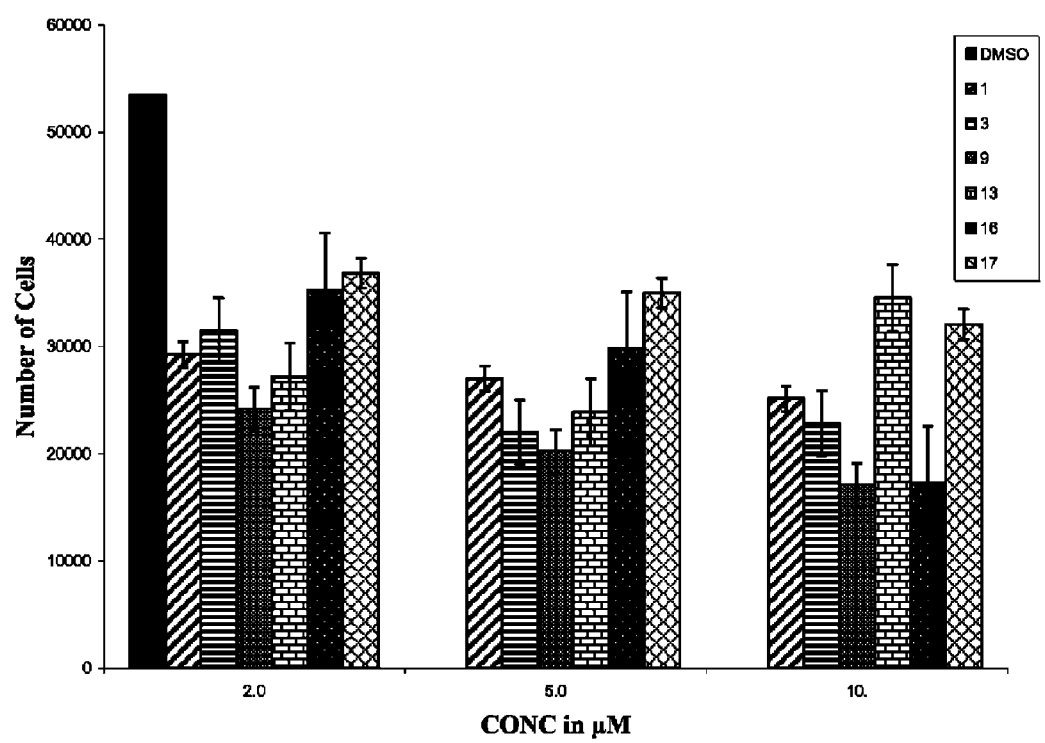
FIG. 3 shows the MTT antiproliferative assay of the most active compounds, Compounds 1, 3, 9, 13, 16, and 17, against the ER-negative human breast cancer cells MDA-MB-231. The results show the number of cells versus the μM concentrations of the compounds.

Utilizing the methods from Example 24 the antiproliferative effects of the compounds were tested against the ER-negative human breast cancer cells MDA-MB-231 Compounds 4-21 showed antiproliferative activity against the MDA-MB-231 cells. Compounds 9, 13, 16, and 17 showed improved activities versus the starting natural products, Compounds 1-3. The most active of those compounds was Compound 9 with an $IC_{50}$ of 5-10 μM. Calculated $IC_{50}$ values are shown in Table 2 below. The advantages of Compound 9 versus its natural parent compound, Compound 3, include more chemical stability, which could impart better metabolic stability, increased polarity, and therefore better water solubility, and it is expected that Compound 9 will have distribution and bioavailability better than that of its natural tocotrienol parent compound. FIG. 3 shows assay results for the most active of the compounds against the ER-negative human breast cancer cells MDA-MB-231 for various micro molar concentrations of the compounds.

TABLE 2

| $IC_{50}$ Values from Examples 2 and 3 | | |
|---|---|---|
| Comp | MCF7 $IC_{50}$ μM | MDA-MB-231 $IC_{50}$ μM |
| 1 | >20 | >10 |
| 2 | 11.4 | >10 |
| 3 | 15.5 | >10 |
| 4 | 4.5 | >10 |
| 5 | >10 | >10 |
| 6 | 6.1 | >10 |
| 7 | 6.1 | >10 |
| 8 | 5.1 | >10 |
| 9 | >10 | 6.6 |
| 10 | 2.4 | >10 |
| 11 | >10 | >10 |
| 12 | >10 | >10 |
| 13 | >20 | >10 |
| 14 | >10 | >10 |
| 15 | >10 | >10 |
| 16 | >20 | 7.2 |

TABLE 2-continued

IC$_{50}$ Values from Examples 2 and 3

| Comp | MCF7 IC$_{50}$ µM | MDA-MB-231 IC$_{50}$ µM |
|---|---|---|
| 17 | >10 | >10 |
| 18 | >10 | >10 |
| 19 | >20 | >10 |
| 20 | >10 | |
| 21 | 5.6 | |

Example 26

Anti-Invasion Assays were performed to measure the anti-invasive properties of Compounds 1-21 using a 96 well basement membrane extract "BME" Cell Invasion Assay (Cultrex®, Trevogen, Catalog# 3455-096-K) with the highly metastatic breast cancer cell line MDA-MB-231. This assay employs a simplified Boyden Chamber design with a polyethylene terephthalate membrane (8 µm). Detection of cell invasion is quantified using calcein-AM. Cells internalize calcein-AM and intracellular esterases cleave the acetomethylester moiety to generate free calcein. Free calcein fluoresces brightly, and this fluorescence may be used to quantify the number of cells that have invaded across BME. (See Tamilarasan and Borghesani, referenced above)

About 504 of basement membrane extract (BME, 1×) coat was added per well. After overnight incubation at 37° C. in a 5% CO$_2$ incubator, 50,000/50 µL of MDA-MB-231 cells in serum free RPMI medium were added to the top chamber of each well, which contained the tested compound at a treatment concentration of 5 µM. About 150 µL of RPMI medium was added to the lower chamber, which contained 10% fetal bovine serum, penicillin/streptomycin, and fibronectin (1 µL/mL) and N-formyl-met-leu-phe (10 nM) as chemoattractants. Cells were allowed to migrate to the lower chamber at 37° C. in a CO$_2$ incubator. After 24 h, the top and bottom chambers were aspirated and washed with a washing buffer solution. About 100 µL of cell dissociation solution/Calcein-AM solution was added to the bottom chamber and incubated for 1 hour at 37° C. in a CO$_2$ incubator. The cells internalized calcein-AM, and the intracellular esterases cleaved the acetomethylester (AM) moiety to generate free calcein. Fluorescence of the samples was determined at 485 nm excitation; 520 nm emissions were measured using a plate reader (BioTek, VT). The numbers of cells that invaded through the BME coat were calculated using a standard curve.

Figure 4:
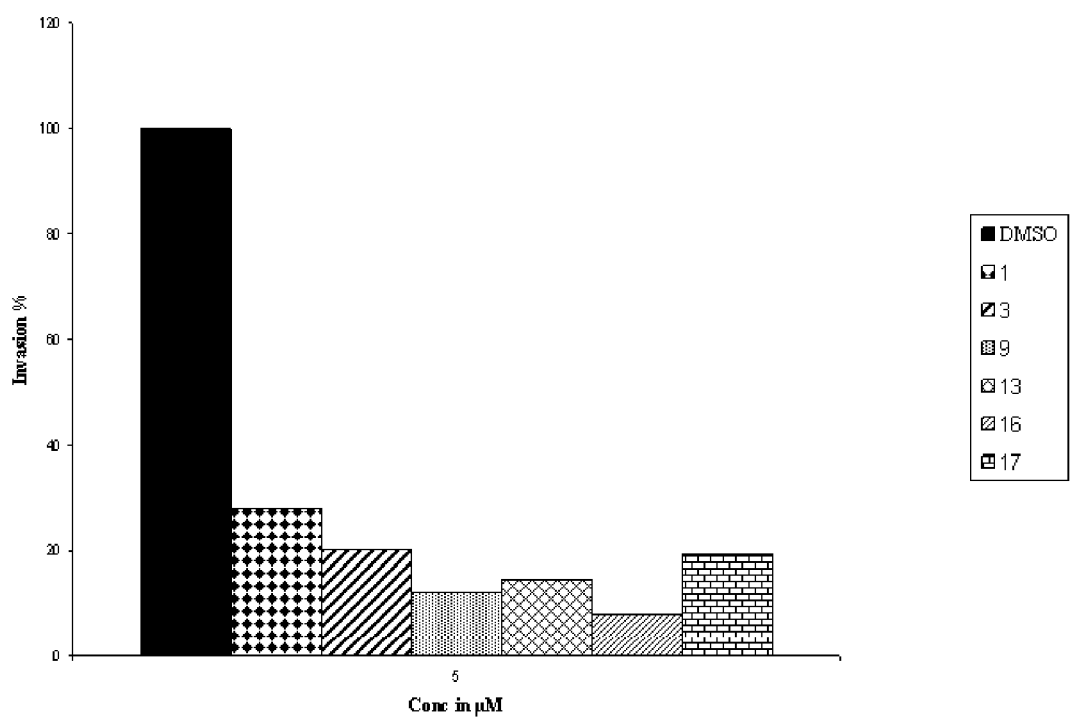
FIG. 4A shows the MTT assay of the anti-invasive activities of the most active compounds, Compounds 1, 3, 9, 13, 16, and 17, against the ER-negative human breast cancer cells MDA-MB-231. The results show the number of cells versus the μM concentrations of the compounds.
Figure 4:
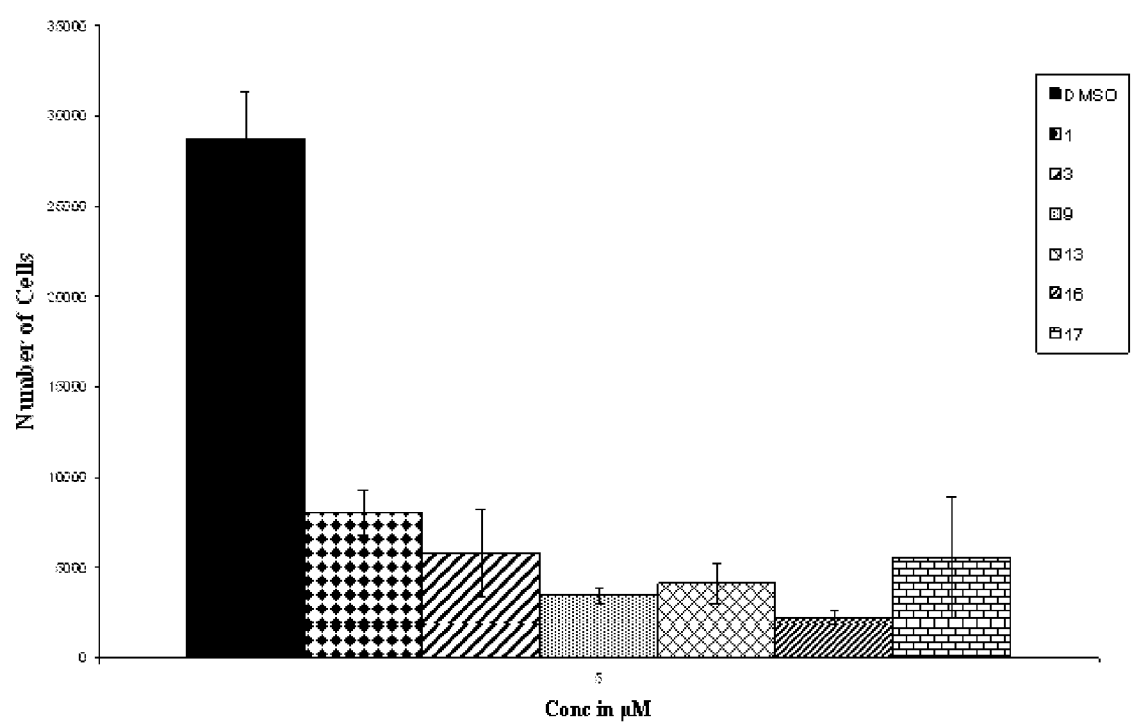

Compounds 1-4, 6, 7-10, and 13-21 showed anti-invasive activity against the ER-negative human breast cancer cells MDA-MB-231. Semisynthetic analogs, Compounds 9, 13, 16, and 17, were more active than their natural tocotrienol parent compounds 1 and 3. The most potent anti-invasive analog was analog 16, allowing only 8% of MDA-MB-231 cells invasion. FIGS. 4A and 4B show the anti-invasive activity of the most active compounds against the ER-negative human breast cancer cells MDA-MB-231 for a 5 micro molar concentration. These results show the potential of these tocotrienol analogs for prevention of breast cancer invasion. This is significant because most cancer mortality is due to metastasis of tumor to distant and vital organs. The therapeutic significance of the demonstrated anti-invasive activity is that inhibition of invasion will inhibit metastasis so that the primary tumors can be treated with chemotherapy, radiotherapy, or surgically removed.

Differences among the various treatment groups were determined by analysis of variance (ANOVA) followed by Dunnett's t-test. Differences were considered to be statistically significant at a value of <0.05, as compared to vehicle treated controls.

Example 27

In a prophetic example, the Beta Tocotrienol Analogs could be used to treat cancer cells according to any of the methods described herein.

Example 28

In a prophetic example, any individual compounds disclosed herein could be administered to a human patient having a need for cancer prevention or treatment by any one of the various known means of drug administration.

As used herein, the term "pharmaceutically acceptable salt" refers to a salt prepared from any one or multiple nontoxic acid(s) or base(s), including both organic and inorganic acids and bases that are suitable for use in contact with living animal or human tissue without causing adverse physiological responses. As used herein, the term "therapeutic amount" indicates an amount which is sufficient to effect beneficial or desired clinical results.

It should be understood that claim limitations pertaining to assays and any other tests are intended to rely on those techniques most prevalent in the art at the time of the earliest priority date of this application which are not inconsistent with the examples disclosed herein. Further, by way of example, language such as "a composition selected from a first therapeutic amount of a compound and a second therapeutic amount of a pharmaceutically acceptable salt of the compound, wherein the compound is selected from: 2,5,7,8-tetramethyl-2-((3E,7E)-4,8,12-trimethyltrideca-3,7,11-trienyl)chroman-6-ylphenylsulfonylcarbamate; 2,7,8-trimethyl-2-((3E,7E)-4,8,12-trimethyltrideca-3,7,11-trienyl)chroman-6-ylphenylsulfonylcarbamate; . . . " in the absence of further explicit limitations is intended to be interpreted to encompass formulations such as those (1) having a therapeutic amount of 2,5,7,8-tetramethyl-2-((3E,7E)-4,8,12-trimethyltrideca-3,7,11-trienyl)chroman-6-ylphenylsulfonylcarbamate as its only active ingredient; and (2) formulations having a therapeutic amount of a pharmaceutically acceptable salt of 2,5,7,8-tetramethyl-2-((3E,7E)-4,8,12-trimethyltrideca-3,7,11-trienyl)chroman-6-ylphenylsulfonylcarbamate regardless of the presence of other related compounds such as 2,7,8-trimethyl-2-((3E,7E)-4,8,12-trimethyltrideca-3,7,11-trienyl)chroman-6-ylphenylsulfonylcarbamate.

As that term is used herein "aromatic" includes for example simple aromatics, substituted aromatics, heteroaromatics, and substituted hetero aromatics. Further the phrase "individual aromatic ring" indicates a five or six membered ring having aromatic properties that optionally shares atoms with another individual aromatic ring of an aromatic.

There are, of course, other alternate embodiments which are obvious from the foregoing descriptions of the invention, which are intended to be included within the scope of the invention, as defined by the following claims.

We claim:

1. A composition of matter comprising a compound selected from:
   2,5,7,8-tetramethyl-2-((3E,7E)-4,8,12-trimethyltrideca-3,7,11-trienyl)chroman-6-ylphenylsulfonylcarbamate;
   2,7,8-trimethyl-2-((3E,7E)-4,8,12-trimethyltrideca-3,7,11-trienyl)chroman-6-ylphenylsulfonylcarbamate;

2,8-dimethyl-2-((3E,7E)-4,8,12-trimethyltrideca-3,7,11-trienyl)chroman-6-ylphenylsulfonylcarbamate;

(R)-2,5,7,8-tetramethyl-2-((3E,7E)-4,8,12-trimethyltrideca-3,7,11-trienyl)chroman-6-yl tosylcarbamate;

(R)-2,7,8-trimethyl-2-((3E,7E)-4,8,12-trimethyltrideca-3,7,11-trienyl)chroman-6-yl tosylcarbamate;

(R)-2,8-dimethyl-2-((3E,7E)-4,8,12-trimethyltrideca-3,7,11-trienyl)chroman-6-yl tosylcarbamate;

(R)-2,5,7,8-tetramethyl-2-((3E,7E)-4,8,12-trimethyltrideca-3,7,11-trienyl)chroman-6-yl 4-chlorophenylsulfonylcarbamate;

(R)-2,7,8-trimethyl-2-((3E,7E)-4,8,12-trimethyltrideca-3,7,11-trienyl)chroman-6-yl 4-chlorophenylsulfonylcarbamate;

(R)-2,8-dimethyl-2-((3E,7E)-4,8,12-trimethyltrideca-3,7,11-trienyl)chroman-6-yl 4-chlorophenylsulfonylcarbamate;

(R)-2,5,7,8-tetramethyl-2-((3E,7E)-4,8,12-trimethyltrideca-3,7,11-trienyl)chroman-6-yl phenylcarbamate;

(R)-2,7,8-trimethyl-2-((3E,7E)-4,8,12-trimethyltrideca-3,7,11-trienyl)chroman-6-yl phenylcarbamate;

(R)-2,8-dimethyl-2-((3E,7E)-4,8,12-trimethyltrideca-3,7,11-trienyl)chroman-6-yl phenylcarbamate;

(R)-2,5,7,8-tetramethyl-2-((3E,7E)-4,8,12-trimethyltrideca-3,7,11-trienyl)chroman-6-yl benzylcarbamate;

(R)-2,7,8-trimethyl-2-((3E,7E)-4,8,12-trimethyltrideca-3,7,11-trienyl)chroman-6-yl benzylcarbamate;

(R)-2,8-dimethyl-2-((3E,7E) 4,8,12-trimethyltrideca-3,7,11-trienyl)chroman-6-yl benzylcarbamate;

(R)-2,5,7,8-tetramethyl-2-((3E,7E)-4,8,12-trimethyltrideca-3,7,11-trienyl)chroman-6-yl benzoylcarbamate;

(R)-2,7,8-trimethyl-2-((3E,7E)-4,8,12-trimethyltrideca-3,7,11-trienyl)chroman-6-yl benzoylcarbamate; and (R)-2,8-dimethyl-2((3E,7E)-4,8,12-trimethyltrideca-3,7,11-trienyl)chroman-6-yl benzoylcarbamate.

2. The composition of matter of claim 1 wherein the compound is 2,5,7,8-tetramethyl-2-((3E,7E)-4,8,12-trimethyltrideca-3,7,11-trienyl)chroman-6-ylphenylsulfonylcarbamate.

3. The composition of matter of claim 1 wherein the compound is 2,7,8-trimethyl-2-((3E,7E)-4,8,12-trimethyltrideca-3,7,11-trienyl)chroman-6-ylphenylsulfonylcarbamate.

4. The composition of matter of claim 1 wherein the compound is 2,8-dimethyl-2-((3E,7E)-4,8,12-trimethyltrideca-3,7,11-trienyl)chroman-6-ylphenylsulfonylcarbamate.

5. The composition of matter of claim 1 wherein the compound is (R)-2,5,7,8-tetramethyl-2-((3E,7E)-4,8,12-trimethyltrideca-3,7,11-trienyl)chroman-6-yl tosylcarbamate.

6. The composition of matter of claim 1 wherein the compound is (R)-2,7,8-trimethyl-2-((3E,7E)-4,8,12-trimethyltrideca-3,7,11-trienyl)chroman-6-yl tosylcarbamate.

7. The composition of matter of claim 1 wherein the compound is (R)-2,8-dimethyl-2-((3E,7E)-4,8,12-trimethyltrideca-3,7,11-trienyl)chroman-6-yl tosylcarbamate.

8. The composition of matter of claim 1 wherein the compound is (R)-2,5,7,8-tetramethyl-2-((3E,7E)-4,8,12-trimethyltrideca-3,7,11-trienyl)chroman-6-yl 4-chlorophenylsulfonylcarbamate.

9. The composition of matter of claim 1 wherein the compound is (R)-2,7,8-trimethyl-2-((3E,7E)-4,8,12-trimethyltrideca-3,7,11-trienyl)chroman-6-yl 4-chlorophenylsulfonylcarbamate.

10. The composition of matter of claim 1 wherein the compound is (R)-2,8-dimethyl-2-((3E,7E)-4,8,12-trimethyltrideca-3,7,11-trienyl)chroman-6-yl 4-chlorophenylsulfonylcarbamate.

11. The composition of matter of claim 1 wherein the compound is (R)-2,5,7,8-tetramethyl-2-((3E,7E)-4,8,12-trimethyltrideca-3,7,11-trienyl)chroman-6-yl phenylcarbamate.

12. The composition of matter of claim 1 wherein the compound is (R)-2,7,8-trimethyl-2-((3E,7E)-4,8,12-trimethyltrideca-3,7,11-trienyl)chroman-6-yl phenylcarbamate.

13. The composition of matter of claim 1 wherein the compound is (R)-2,8-dimethyl-2-((3E,7E)-4,8,12-trimethyltrideca-3,7,11-trienyl)chroman-6-yl phenylcarbamate.

14. The composition of matter of claim 1 wherein the compound is (R)-2,5,7,8-tetramethyl-2-((3E,7E)-4,8,12-trimethyltrideca-3,7,11-trienyl)chroman-6-yl benzylcarbamate.

15. The composition of matter of claim 1 wherein the compound is (R)-2,7,8-trimethyl-2-((3E,7E)-4,8,12-trimethyltrideca-3,7,11-trienyl)chroman-6-yl benzylcarbamate.

16. The composition of matter of claim 1 wherein the compound is (R)-2,8-dimethyl-2-((3E,7E) 4,8,12-trimethyltrideca-3,7,11-trienyl)chroman-6-yl benzylcarbamate.

17. The composition of matter of claim 1 wherein the compound is (R)-2,5,7,8-tetramethyl-2-((3E,7E)-4,8,12-trimethyltrideca-3,7,11-trienyl)chroman-6-yl benzoylcarbamate.

18. The composition of matter of claim 1 wherein the compound is (R)-2,7,8-trimethyl-2-((3E,7E)-4,8,12-trimethyltrideca-3,7,11-trienyl)chroman-6-yl benzoylcarbamate.

19. The composition of matter of claim 1 wherein the compound is (R)-2,8-dimethyl-2-((3E,7E)-4,8,12-trimethyltrideca-3,7,11-trienyl)chroman-6-yl benzoylcarbamate.

20. A composition of matter comprising a compound having the general formula:

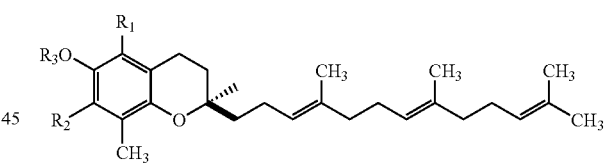

wherein $R_1$ is either H or $CH_3$;

wherein $R_2$ is either H or $CH_3$; and wherein $R_3$ is a functional group that causes the compound to be classified as a carbamate;

wherein the molecular weight of the compound is at most 621.35.

21. The composition of matter of claim 20 wherein the functional group is:

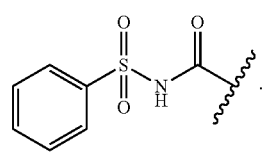

22. The composition of matter of claim 20 wherein the functional group is:

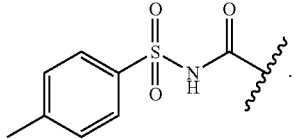
b

23. The composition of matter of claim 20 wherein the functional group is:

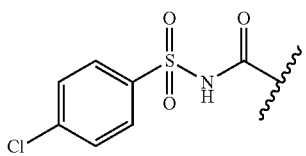
c

24. The composition of matter of claim 20 wherein the functional group is:

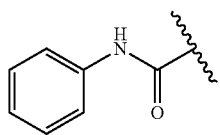
d

25. The composition of matter of claim 20 wherein the functional group is:

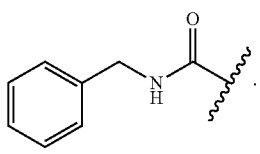
e

26. The composition of matter of claim 20 wherein the functional group is:

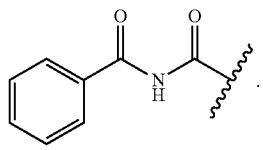
f

27. The composition of matter of claim 20 wherein the functional group contains an aromatic ring.

28. The composition of matter of claim 20 wherein the compound is a carbamate.

29. The composition of matter of claim 20 wherein the compound is a tocotrienol-6-O-carbamate.

30. The composition of matter of claim 20 wherein the compound has a polarity greater than or equal to the polarity of α-tocotrienol.

31. The composition of matter of claim 20 wherein the compound has a polarity less than or equal to the polarity of γ-tocotrienol.

32. The composition of matter of claim 20 wherein the molecular weight of the compound is at least 515.34.

33. The composition of matter of claim 20 wherein the functional group contains a sulfur atom.

34. A method of treating a form of cancer comprising administering to a mammalian patient in need of the treatment a composition selected from a first therapeutic amount of a compound and a second therapeutic amount of a pharmaceutically acceptable salt of the compound, wherein the form of cancer is breast cancer and wherein the compound is selected from:
  2,5,7,8-tetramethyl-2-((3E,7E)-4,8,12-trimethyltrideca-3,7,11-trienyl)chroman-6-ylphenylsulfonylcarbamate;
  2,7,8-trimethyl-2-((3E,7E)-4,8,12-trimethyltrideca-3,7,11-trienyl)chroman -6-ylphenylsulfonylcarbamate;
  2,8-dimethyl-2-((3E,7E)-4,8,12-trimethyltrideca-3,7,11-trienyl)chroman-6-ylphenylsulfonylcarbamate;
  (R)-2,5,7,8-tetramethyl-2-((3E,7E)-4,8,12-trimethyltrideca-3,7,11-trienyl)chroman-6-yl tosylcarbamate;
  (R)-2,7,8-trimethyl-2-((3E,7E)-4,8,12-trimethyltrideca-3,7,11-trienyl)chroman-6-yl tosylcarbamate;
  (R)-2,8-dimethyl-2-((3E,7E)-4,8,12-trimethyltrideca-3,7,11-trienyl)chroman-6-yl tosylcarbamate;
  (R)-2,5,7,8-tetramethyl-2-((3E,7E)-4,8,12-trimethyltrideca-3,7,11-trienyl)chroman-6-yl 4-chlorophenylsulfonylcarbamate;
  (R)-2,7,8-trimethyl-2-((3E,7E)-4,8,12-trimethyltrideca-3,7,11-trienyl)chroman-6-yl 4-chlorophenylsulfonylcarbamate;
  (R)-2,8-dimethyl-2-((3E,7E)-4,8,12-trimethyltrideca-3,7,11-trienyl)chroman-6-yl 4-chlorophenylsulfonylcarbamate;
  (R)-2,5,7,8-tetramethyl-2-((3E,7E)-4,8,12-trimethyltrideca-3,7,11-trienyl)chroman-6-yl phenylcarbamate;
  (R)-2,7,8-trimethyl-2-((3E,7E)-4,8,12-trimethyltrideca-3,7,11-trienyl)chroman-6-yl phenylcarbamate;
  (R)-2,8-dimethyl-2-((3E,7E)-4,8,12-trimethyltrideca-3,7,11-trienyl)chroman-6-yl phenylcarbamate;
  (R)-2,5,7,8-tetramethyl-2-((3E,7E)-4,8,12-trimethyltrideca-3,7,11-trienyl)chroman-6-yl benzylcarbamate;
  (R)-2,7,8-trimethyl-2-((3E,7E)-4,8,12-trimethyltrideca-3,7,11-trienyl)chroman-6-yl benzylcarbamate;
  (R)-2,8-dimethyl-2-((3E,7E) 4,8,12-trimethyltrideca-3,7,11-trienyl)chroman-6-yl benzylcarbamate;
  (R)-2,5,7,8-tetramethyl-2-((3E,7E)-4,8,12-trimethyltrideca-3,7,11-trienyl)chroman-6-ylbenzoylcarbamate;
  (R)-2,7,8-trimethyl-2-((3E,7E)-4,8,12-trimethyltrideca-3,7,11-trienyl)chroman-6-yl benzoylcarbamate; and
  (R)-2,8-dimethyl-2-((3E,7E)-4,8,12-trimethyltrideca-3,7,11-trienyl)chroman-6-yl benzoylcarbamate.

35. The method of claim 34 wherein the compound is 2,5,7,8-tetramethyl-2-((3E,7E)-4,8,12-trimethyltrideca-3,7,11-trienyl)chroman-6-ylphenylsulfonylcarbamate.

36. The method of claim 34 wherein the compound is 2,7,8-trimethyl-2-((3E,7E)-4,8,12-trimethyltrideca-3,7,11-trienyl)chroman-6-ylphenylsulfonylcarbamate.

37. The method of claim 34 wherein the compound is 2,8-dimethyl -2-((3E,7E)-4,8,12-trimethyltrideca-3,7,11-trienyl)chroman-6-ylphenylsulfonylcarbamate.

38. The method of claim 34 wherein the compound is (R)-2,5,7,8-tetramethyl-2-((3E,7E)-4,8,12-trimethyltrideca-3,7,11-trienyl)chroman-6-yl tosylcarbamate.

39. The method of claim 34 wherein the compound is (R)-2,7,8-trimethyl-2-((3E,7E)-4,8,12-trimethyltrideca-3,7,11-trienyl)chroman-6-yl tosylcarbamate.

40. The method of claim 34 wherein the compound is (R)-2,8-dimethyl-2-((3E,7E)-4,8,12-trimethyltrideca-3,7,11-trienyl)chroman-6-yl tosylcarbamate.

41. The method of claim 34 wherein the compound is (R)-2,5,7,8-tetramethyl-2-((3E,7E)-4,8,12-trimethyltrideca-3,7,11-trienyl)chroman-6-yl 4-chlorophenylsulfonylcarbamate.

42. The method of claim 34 wherein the compound is (R)-2,7,8-trimethyl-2-((3E,7E)-4,8,12-trimethyltrideca-3,7,11-trienyl)chroman-6-yl 4-chlorophenylsulfonylcarbamate.

43. The method of claim 34 wherein the compound is (R)-2,8-dimethyl-2-((3E,7E)-4,8,12-trimethyltrideca-3,7,11-trienyl)chroman-6-yl 4-chlorophenylsulfonylcarbamate.

44. The method of claim 34 wherein the compound is (R)-2,5,7,8-tetramethyl-2-((3E,7E)-4,8,12-trimethyltrideca-3,7,11-trienyl)chroman-6-yl phenylcarbamate.

45. The method of claim 34 wherein the compound is (R)-2,7,8-trimethyl-2-((3E,7E)-4,8,12-trimethyltrideca-3,7,11-trienyl)chroman-6-yl phenylcarbamate.

46. The method of claim 34 wherein the compound is (R)-2,8-dimethyl-2-((3E,7E)-4,8,12-trimethyltrideca-3,7,11-trienyl)chroman-6-yl phenylcarbamate.

47. The method of claim 34 wherein the compound is (R)-2,5,7,8-tetramethyl-2-((3E,7E)-4,8,12-trimethyltrideca-3,7,11-trienyl)chroman-6-yl benzylcarbamate.

48. The method of claim 34 wherein the compound is (R)-2,7,8-trimethyl-2-((3E,7E)-4,8,12-trimethyltrideca-3,7,11-trienyl)chroman-6-yl benzylcarbamate.

49. The method of claim 34 wherein the compound is (R)-2,8-dimethyl-2-((3E,7E) 4,8,12-trimethyltrideca-3,7,11-trienyl)chroman-6-yl benzylcarbamate.

50. The method of claim 34 wherein the compound is (R)-2,5,7,8-tetramethyl-2-((3E,7E)-4,8,12-trimethyltrideca-3,7,11-trienyl)chroman-6-yl benzoylcarbamate.

51. The method of claim 34 wherein the compound is (R)-2,7,8-trimethyl-2-((3E,7E)-4,8,12-trimethyltrideca-3,7,11-trienyl)chroman-6-yl benzoylcarbamate.

52. The method of claim 34 wherein the compound is (R)-2,8-dimethyl-2-((3E,7E)-4,8,12-trimethyltrideca-3,7,11-trienyl)chroman-6-yl benzoylcarbamate.

53. The method of claim 34 wherein the mammalian patient is a human.

54. A method of treating a form of cancer comprising exposing a mammalian cell to a composition selected from a first therapeutic amount of a compound and a second therapeutic amount of a pharmaceutically acceptable salt of the compound, wherein the mammalian cell is a breast cancer cell and wherein the compound is selected from:

2,5,7,8-tetramethyl-2-((3E,7E)-4,8,12-trimethyltrideca-3,7,11-trienyl)chroman-6-ylphenylsulfonylcarbamate;

2,7,8-trimethyl-2-((3E,7E)-4,8,12-trimethyltrideca-3,7,11-trienyl)chroman -6-ylphenylsulfonylcarbamate;

2,8-dimethyl-2-((3E,7E)-4,8,12-trimethyltrideca-3,7,11-trienyl)chroman-6-ylphenylsulfonylcarbamate;

(R)-2,5,7,8-tetramethyl-2-((3E,7E)-4,8,12-trimethyltrideca-3,7,11-trienyl)chroman-6-yl tosylcarbamate;

(R)-2,7,8-trimethyl-2-((3E,7E)-4,8,12-trimethyltrideca-3,7,11-trienyl)chroman-6-yl tosylcarbamate;

(R)-2,8-dimethyl-2-((3E,7E)-4,8,12-trimethyltrideca-3,7,11-trienyl)chroman-6-yl tosylcarbamate;

(R)-2,5,7,8-tetramethyl-2-((3E,7E)-4,8,12-trimethyltrideca-3,7,11-trienyl)chroman-6-yl 4-chlorophenylsulfonylcarbamate;

(R)-2,7,8-trimethyl-2-((3E,7E)-4,8,12-trimethyltrideca-3,7,11-trienyl)chroman-6-yl 4-chlorophenylsulfonylcarbamate;

(R)-2,8-dimethyl-2-((3E,7E)-4,8,12-trimethyltrideca-3,7,11-trienychroman-6-yl 4-chlorophenylsulfonylcarbamate;

(R)-2,5,7,8-tetramethyl-2-((3E,7E)-4,8,12-trimethyltrideca-3,7,11-trienyl)chroman-6-yl phenylcarbamate;

(R)-2,7,8-trimethyl-2-((3E,7E)-4,8,12-trimethyltrideca-3,7,11-trienyl)chroman-6-yl phenylcarbamate;

(R)-2,8-dimethyl-2-((3E,7E)-4,8,12-trimethyltrideca-3,7,11-trienyl)chroman-6-yl phenylcarbamate;

(R)-2,5,7,8-tetramethyl-2-((3E,7E)-4,8,12-trimethyltrideca-3,7,11-trienyl)chroman-6-yl benzylcarbamate;

(R)-2,7,8-trimethyl-2-((3E,7E)-4,8,12-trimethyltrideca-3,7,11-trienyl)chroman-6-yl benzylcarbamate;

(R)-2,8-dimethyl-2-((3E,7E) 4,8,12-trimethyltrideca-3,7,11-trienyl)chroman-6-yl benzylcarbamate;

(R)-2,5,7,8-tetramethyl-2-((3E,7E)-4,8,12-trimethyltrideca-3,7,11-trienyl)chroman-6-yl benzoylcarbamate;

(R)-2,7,8-trimethyl-2-((3E,7E)-4,8,12-trimethyltrideca-3,7,11-trienyl)chroman-6-ylbenzoylcarbamate; and (R)-2,8-dimethyl-2-((3E,7E)-4,8,12-trimethyltrideca-3,7,11-trienyl)chroman-6-yl benzoylcarbamate.

55. The method of claim 54 wherein the compound is 2,5,7,8-tetramethyl-2-((3E,7E)-4,8,12-trimethyltrideca-3,7,11-trienyl)chroman-6-ylphenylsulfonylcarbamate.

56. The method of claim 54 wherein the compound is 2,7,8-trimethyl-2-((3E,7E)-4,8,12-trimethyltrideca-3,7,11-trienyl)chroman-6-ylphenylsulfonylcarbamate.

57. The method of claim 54 wherein the compound is 2,8-dimethyl -2-((3E,7E)-4,8,12-trimethyltrideca-3,7,11-trienyl)chroman-6-ylphenylsulfonylcarbamate.

58. The method of claim 54 wherein the compound is (R)-2,5,7,8-tetramethyl-2-((3E,7E)-4,8,12-trimethyltrideca-3,7,11-trienyl)chroman-6-yl tosylcarbamate.

59. The method of claim 54 wherein the compound is (R)-2,7,8-trimethyl-2-((3E,7E)-4,8,12-trimethyltrideca-3,7,11-trienyl)chroman-6-yl tosylcarbamate.

60. The method of claim 54 wherein the compound is (R)-2,8-dimethyl-2-((3E,7E)-4,8,12-trimethyltrideca-3,7,11-trienyl)chroman-6-yl tosylcarbamate.

61. The method of claim 54 wherein the compound is (R)-2,5,7,8-tetramethyl-2-((3E,7E)-4,8,12-trimethyltrideca-3,7,11-trienyl)chroman-6-yl 4-chlorophenylsulfonylcarbamate.

62. The method of claim 54 wherein the compound is (R)-2,7,8-trimethyl-2-((3E,7E)-4,8,12-trimethyltrideca-3,7,11-trienyl)chroman-6-yl 4-chlorophenylsulfonylcarbamate.

63. The method of claim 54 wherein the compound is (R)-2,8-dimethyl-2-((3E,7E)-4,8,12-trimethyltrideca-3,7,11-trienyl)chroman-6-yl 4-chlorophenylsulfonylcarbamate.

64. The method of claim 54 wherein the compound is (R)-2,5,7,8-tetramethyl-2-((3E,7E)-4,8,12-trimethyltrideca-3,7,11-trienyl)chroman-6-yl phenylcarbamate.

65. The method of claim 54 wherein the compound is (R)-2,7,8-trimethyl-2-((3E,7E)-4,8,12-trimethyltrideca-3,7,11-trienyl)chroman-6-yl phenylcarbamate.

66. The method of claim 54 wherein the compound is (R)-2,8-dimethyl-2-((3E,7E)-4,8,12-trimethyltrideca-3,7,11-trienyl)chroman-6-yl phenylcarbamate.

67. The method of claim 54 wherein the compound is (R)-2,5,7,8-tetramethyl-2-((3E,7E)-4,8,12-trimethyltrideca-3,7,11-trienyl)chroman-6-yl benzylcarbamate.

68. The method of claim 54 wherein the compound is (R)-2,7,8-trimethyl-2-((3E,7E)-4,8,12-trimethyltrideca-3,7,11-trienyl)chroman-6-yl benzylcarbamate.

69. The method of claim 54 wherein the compound is (R)-2,8-dimethyl-2-((3E,7E) 4,8,12-trimethyltrideca-3,7,11-trienyl)chroman-6-yl benzylcarbamate.

70. The method of claim 54 wherein the compound is (R)-2,5,7,8-tetramethyl-2-((3E,7E)-4,8,12-trimethyltrideca-3,7,11-trienyl)chroman-6-yl benzoylcarbamate.

71. The method of claim 54 wherein the compound is (R)-2,7,8-trimethyl-2-((3E,7E)-4,8,12-trimethyltrideca-3,7,11-trienyl)chroman-6-yl benzoylcarbamate.

72. The method of claim 54 wherein the compound is (R)-2,8-dimethyl-2-((3E,7E)-4,8,12-trimethyltrideca-3,7,11-trienyl)chroman-6-yl benzoylcarbamate.

73. The method of claim 54 wherein the mammalian cell is a cancerous cell.

74. The method of claim 54 wherein the mammalian cell is a human cell.

75. The method of claim 54 wherein the mammalian patient is a human.

76. The composition of matter of claim 20 wherein the functional group is a group imparting greater water solubility to the compound than the natural tocotrienol having the same $R_1$ and $R_2$ groups.

77. An in vivo product produced by a process comprising administering a pharmacological composition to a mammalian patient by a form of delivery selected from: intravenous, intraperitoneal, subcutaneous, intramuscular, ocular, oral, transdermal, topical and inhalation wherein the in vivo product is present in a therapeutic amount wherein the pharmacological composition is selected from:

2,5,7,8-tetramethyl-2-((3E,7E)-4,8,12-trimethyltrideca-3,7,11-trienyl)chroman-6-ylphenylsulfonylcarbamate;

2,7,8-trimethyl-2-((3E,7E)-4,8,12-trimethyltrideca-3,7,11-trienyl)chroman -6-ylphenylsulfonylcarbamate;

2,8-dimethyl-2-((3E,7E)-4,8,12-trimethyltrideca-3,7,11-trienyl)chroman-6-ylphenylsulfonylcarbamate;

(R)-2,5,7,8-tetramethyl-2-((3E,7E)-4,8,12-trimethyltrideca-3,7,11-trienyl)chroman-6-yl tosylcarbamate;

(R)-2,7,8-trimethyl-2-((3E,7E)-4,8,12-trimethyltrideca-3,7,11-trienyl)chroman-6-yl tosylcarbamate;

(R)-2,8-dimethyl-2-((3E,7E)-4,8,12-trimethyltrideca-3,7,11-trienyl)chroman-6-yl tosylcarbamate;

(R)-2,5,7,8-tetramethyl-2-((3E,7E)-4,8,12-trimethyltrideca-3,7,11-trienyl)chroman-6-yl 4-chlorophenylsulfonylcarbamate;

(R)-2,7,8-trimethyl-2-((3E,7E)-4,8,12-trimethyltrideca-3,7,11-trienyl)chroman-6-yl 4-chlorophenylsulfonylcarbamate;

(R)-2,8-dimethyl-2-((3E,7E)-4,8,12-trimethyltrideca-3,7,11-trienyl)chroman-6-yl 4-chlorophenylsulfonylcarbamate;

(R)-2,5,7,8-tetramethyl-2-((3E,7E)-4,8,12-trimethyltrideca-3,7,11-trienyl)chroman-6-yl phenylcarbamate;

(R)-2,7,8-trimethyl-2-((3E,7E)-4,8,12-trimethyltrideca-3,7,11-trienyl)chroman-6-yl phenylcarbamate;

(R)-2,8-dimethyl-2-((3E,7E)-4,8,12-trimethyltrideca-3,7,11-trienyl)chroman-6-yl phenylcarbamate;

(R)-2,5,7,8-tetramethyl-2-((3E,7E)-4,8,12-trimethyltrideca-3,7,11-trienyl)chroman-6-yl benzylcarbamate;

(R)-2,7,8-trimethyl-2-((3E,7E)-4,8,12-trimethyltrideca-3,7,11-trienyl)chroman-6-yl benzylcarbamate;

(R)-2,8-dimethyl-2-((3E,7E) 4,8,12-trimethyltrideca-3,7,11-trienyl)chroman-6-yl benzylcarbamate;

(R)-2,5,7,8-tetramethyl-2-((3E,7E)-4,8,12-trimethyltrideca-3,7,11-trienyl)chroman-6-yl benzoylcarbamate;

(R)-2,7,8-trimethyl-2-((3E,7E)-4,8,12-trimethyltrideca-3,7,11-trienyl)chroman-6-yl benzoylcarbamate; and (R)-2,8-dimethyl-2-((3E,7E)-4,8,12-trimethyltrideca-3,7,11-trienyl)chroman-6-yl benzoylcarbamate.

78. The composition of matter of claim 77 wherein the compound is 2,5,7,8-tetramethyl-2-((3E,7E)-4,8,12-trimethyltrideca-3,7,11-trienyl)chroman-6-ylphenylsulfonylcarbamate.

79. The composition of matter of claim 77 wherein the compound is 2,7,8-trimethyl-2-((3E,7E)-4,8,12-trimethyltrideca-3,7,11-trienyl)chroman -6-ylphenylsulfonylcarbamate.

80. The composition of matter of claim 77 wherein the compound is 2,8-dimethyl-2-((3E,7E)-4,8,12-trimethyltrideca-3,7,11-trienyl)chroman-6-ylphenylsulfonylcarbamate.

81. The composition of matter of claim 77 wherein the compound is (R)-2,5,7,8-tetramethyl-2-((3E,7E)-4,8,12-trimethyltrideca-3,7,11-trienyl)chroman-6-yl tosylcarbamate.

82. The composition of matter of claim 77 wherein the compound is (R)-2,7,8-trimethyl-2-((3E,7E)-4,8,12-trimethyltrideca-3,7,11-trienyl)chroman-6-yl tosylcarbamate.

83. The composition of matter of claim 77 wherein the compound is (R)-2,8-dimethyl-2-((3E,7E)-4,8,12-trimethyltrideca-3,7,11-trienyl)chroman-6-yl tosylcarbamate.

84. The composition of matter of claim,77 wherein the compound is (R)-2,5,7,8-tetramethyl-2-((3E,7E)-4,8,12-trimethyltrideca-3,7,11-trienyl)chroman-6-yl 4-chlorophenylsulfonylcarbamate.

85. The composition of matter of claim 77 wherein the compound is (R)-2,7,8-trimethyl-2-((3E,7E)-4,8,12-trimethyltrideca-3,7,11-trienyl)chroman-6-yl 4-chlorophenylsulfonylcarbamate.

86. The composition of matter of claim 77 wherein the compound is (R)-2,8-dimethyl-2-((3E,7E)-4,8,12-trimethyltrideca-3,7,11-trienyl)chroman-6-yl 4-chlorophenylsulfonylcarbamate.

87. The composition of matter of claim 77 wherein the compound is (R)-2,5,7,8-tetramethyl-2-((3E,7E)-4,8,12-trimethyltrideca-3,7,11-trienyl)chroman-6-yl phenylcarbamate.

88. The composition of matter of claim 77 wherein the compound is (R)-2,7,8-tri methyl-2-((3E,7E)-4,8,12-trimethyltrideca-3,7,11-trienyl)chroman-6-yl phenylcarbamate.

89. The composition of matter of claim 77 wherein the compound is (R)-2,8-dimethyl-2-((3E,7E)-4,8,12-trimethyltrideca-3,7,11-trienyl)chroman-6-yl phenylcarbamate.

90. The composition of matter of claim 77 wherein the compound is (R)-2,5,7,8-tetramethyl-2-((3E,7E)-4,8,12-trimethyltrideca-3,7,11-trienyl)chroman-6-yl benzylcarbamate.

91. The composition of matter of claim 77 wherein the compound is (R)-2,7,8-trimethyl-2-((3E,7E)-4,8,12-trimethyltrideca-3,7,11-trienyl)chroman-6-yl benzylcarbamate.

92. The composition of matter of claim 77 wherein the compound is (R)-2,8-dimethyl-2-((3E,7E) 4,8,12-trimethyltrideca-3,7,11-trienyl)chroman-6-yl benzylcarbamate.

93. The composition of matter of claim 77 wherein the compound is (R)-2,5,7,8-tetramethyl-2-((3E,7E)-4,8,12-trimethyltrideca -3,7,11-trienyl)chroman-6-yl benzoylcarbamate.

94. The composition of matter of claim 77 wherein the compound is (R)-2,7,8-trimethyl-2-((3E,7E)-4,8,12-trimethyltrideca -3,7,11-trienyl)chroman-6-yl benzoylcarbamate.

95. The composition of matter of claim 77 wherein the compound is (R)-2,8-dimethyl-2-((3E,7E)-4,8,12-trimethyltrideca-3,7,11-trienyl)chroman-6-yl benzoylcarbamate.

96. A method of treating a form of cancer comprising directing a human patient to internalize a composition of matter selected from a first therapeutic amount of a compound and a second therapeutic amount of a pharmaceutically acceptable salt of the compound, wherein the form of cancer is breast cancer and wherein the compound is selected from:
- 2,5,7,8-tetramethyl-2-((3E,7E)-4,8,12-trimethyltrideca-3,7,11-trienyl)chroman-6-ylphenylsulfonylcarbamate;
- 2,7,8-trimethyl-2-((3E,7E)-4,8,12-trimethyltrideca-3,7,11-trienyl)chroman-6-ylphenylsulfonylcarbamate;
- 2,8-dimethyl-2-((3E,7E)-4,8,12-trimethyltrideca-3,7,11-trienyl)chroman-6-ylphenylsulfonylcarbamate;
- (R)-2,5,7,8-tetramethyl-2-((3E,7E)-4,8,12-trimethyltrideca -3,7,11-trienyl)chroman-6-yl tosylcarbamate;
- (R)-2,7,8-trimethyl-2-((3E,7E)-4,8,12-trimethyltrideca-3,7,11-trienyl)chroman-6-yl tosylcarbamate;
- (R)-2,8-dimethyl-2-((3E,7E)-4,8,12-trimethyltrideca-3,7,11-trienyl)chroman-6-yl tosylcarbamate;
- (R)-2,5,7,8-tetramethyl-2-((3E,7E)-4,8,12-trimethyltrideca -3,7,11-trienyl)chroman-6-yl 4-chlorophenylsulfonylcarbamate;
- (R)-2,7,8-trimethyl-2-((3E,7E)-4,8,12-trimethyltrideca-3,7,11-trienyl)chroman-6-yl 4-chlorophenylsulfonylcarbamate;
- (R)-2,8-dimethyl-2-((3E,7E)-4,8,12-trimethyltrideca-3,7,11-trienyl)chroman-6-yl 4-chlorophenylsulfonylcarbamate;
- (R)-2,5,7,8-tetramethyl-2-((3E,7E)-4,8,12-trimethyltrideca -3,7,11-trienyl)chroman-6-yl phenylcarbamate;
- (R)-2,7,8-trimethyl-2-((3E,7E)-4,8,12-trimethyltrideca-3,7,11-trienyl)chroman-6-yl phenylcarbamate;
- (R)-2,8-dimethyl-2-((3E,7E)-4,8,12-trimethyltrideca-3,7,11-trienyl)chroman-6-yl phenylcarbamate;
- (R)-2,5,7,8-tetramethyl-2-((3E,7E)-4,8,12-trimethyltrideca -3,7,11-trienyl)chroman-6-yl benzylcarbamate;
- (R)-2,7,8-trimethyl-2-((3E,7E)-4,8,12-trimethyltrideca-3,7,11-trienyl)chroman-6-yl benzylcarbamate;
- (R)-2,8-dimethyl-2-((3E,7E) 4,8,12-trimethyltrideca-3,7,11-trienyl)chroman-6-yl benzylcarbamate;
- (R)-2,5,7,8-tetramethyl-2-((3E,7E)-4,8,12-trimethyltrideca -3,7,11-trienyl)chroman-6-yl benzoylcarbamate;
- (R)-2,7,8-trimethyl-2-((3E,7E)-4,8,12-trimethyltrideca-3,7,11-trienyl)chroman-6-yl benzoylcarbamate; and
- (R)-2,8-dimethyl-2-((3E,7E)-4,8,12-trimethyltrideca-3,7,11-trienyl)chroman-6-yl benzoylcarbamate; and performing an assessment step selected from identifying the form of cancer, quantifying the form of cancer, and characterizing the form of cancer based on information from a test step selected from: a biopsy, an endoscopy, a bronchoscopy, a nasendoscopy; a X-ray, a CT scan, an MRI scan, an ultrasound, a scintigraphy, a single photon emission computed tomography, a positron emission tomography, and a blood test.

97. The method of claim 96 wherein the test step consists of a blood test.

98. The method of claim 96 wherein the compound is 2,5,7,8-tetramethyl-2-((3E,7E)-4,8,12-trimethyltrideca-3,7,11-trienyl)chroman-6-ylphenylsulfonylcarbamate.

99. The method of claim 96 wherein the compound is 2,7,8-trimethyl-2-((3E,7E)-4,8,12-trimethyltrideca-3,7,11-trienyl)chroman-6-ylphenylsulfonylcarbamate.

100. The method of claim 96 wherein the compound is 2,8-dimethyl-2-((3E,7E)-4,8,12-trimethyltrideca-3,7,11-trienyl)chroman-6-ylphenylsulfonylcarbamate.

101. The method of claim 96 wherein the compound is (R)-2,5,7,8-tetramethyl-2-((3E,7E)-4,8,12-trimethyltrideca-3,7,11-trienyl)chroman-6-yl tosylcarbamate.

102. The method of claim 96 wherein the compound is (R)-2,7,8-trimethyl-2-((3E,7E)-4,8,12-trimethyltrideca-3,7,11-trienyl)chroman -6-yl tosylcarbamate.

103. The method of claim 96 wherein the compound is (R)-2,8-dimethyl-2-((3E,7E)-4,8,12-trimethyltrideca-3,7,11-trienyl)chroman-6-y1 tosylcarbamate.

104. The method of claim 96 wherein the compound is (R)-2,5,7,8-tetramethyl-2-((3E,7E)-4,8,12-trimethyltrideca-3,7,11-trienyl)chroman-6-yl 4-chlorophenylsulfonylcarbamate.

105. The method of claim 96 wherein the compound is (R)-2,7,8-trimethyl-2-((3E,7E)-4,8,12-trimethyltrideca-3,7,11-trienyl)chroman -6-yl 4-chlorophenylsulfonylcarbamate.

106. The method of claim 96 wherein the compound is (R)-2,8-dim ethyl-2-((3E,7E)-4,8,12-trimethyltridec a-3,7,11-trienyl)chrom an-6-yl 4-chlorophenylsulfonylcarbamate.

107. The method of claim 96 wherein the compound is (R)-2,5,7,8-tetramethyl-2-((3E,7E)-4,8,12-trimethyltrideca-3,7,11-trienyl)chroman-6-yl phenylcarbamate.

108. The method of claim 96 wherein the compound is (R)-2,7,8-trimethyl-2-((3E,7E)-4,8,12-trimethyltrideca-3,7,11-trienyl)chroman -6-yl phenylcarbamate.

109. The method of claim 96 wherein the compound is (R)-2,8-dimethyl-2-((3E,7E)-4,8,12-trimethyltrideca-3,7,11-trienyl)chroman-6-yl phenylcarbamate.

110. The method of claim 96 wherein the compound is (R)-2,5,7,8-tetramethyl-2-((3E,7E)-4,8,12-trimethyltrideca-3,7,11-trienyl)chroman-6-yl benzylcarbamate.

111. The method of claim 96 wherein the compound is (R)-2,7,8-trimethyl-2-((3E,7E)-4,8,12-trimethyltrideca-3,7,11-trienyl)chroman -6-yl benzylcarbamate.

112. The method of claim 96 wherein the compound is (R)-2,8-dimethyl-2-((3E,7E) 4,8,12-trimethyltrideca-3,7,11-trienyl)chroman-6-yl benzylcarbamate.

113. The method of claim 96 wherein the compound is (R)-2,5,7,8-tetramethyl-2-((3E,7E)-4,8,12-trimethyltrideca-3,7,11-trienyl)chroman-6-yl benzoylcarbamate.

114. The method of claim 96 wherein the compound is (R)-2,7,8-triinethyl-2-((3E,7E)-4,8,12-trimethyltrideca-3,7,11-trienyl)chroman -6-yl benzoylcarbamate.

115. The method of claim 96 wherein the compound is (R)-2,8-dimethyl-2-((3E,7E)-4,8,12-trimethyltride c a-3,7,11-trienyl)chrom an-6-yl benzoylcarbamate.

116. A composition of matter comprising a compound represented by the combination of a general formula represented by

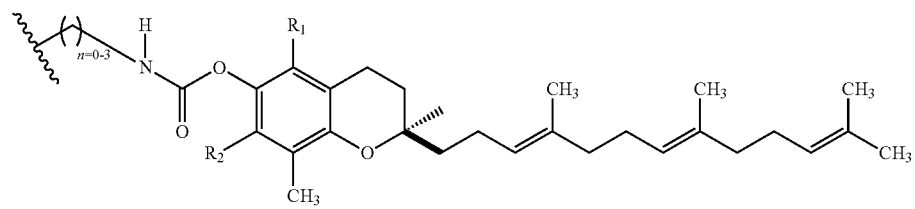

and a functional group selected from

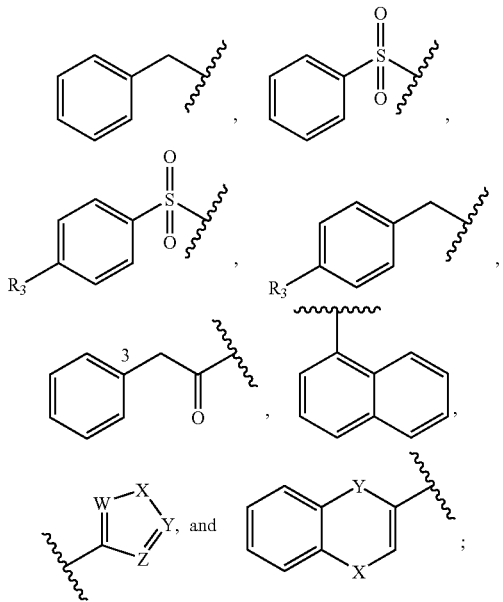

wherein $R_1$ is selected from H and $CH_3$;
wherein $R_2$ is selected from H and $CH_3$;
wherein $R_3$ is selected from $CH_3$ $C_2H_5$, isopropyl, n-propyl, n-butyl, t-butyl, and isobutyl;
wherein W is selected from O, N, S, and C;
wherein X is selected from O, N, S, and C;
wherein Y is selected from O, N, S, and C; and
wherein Z is selected from O, N, S, and C.

117. A composition of matter comprising a pharmaceutically acceptable salt of a compound selected from:
2,5,7,8-tetramethyl-2-((3E,7E)-4,8,12-trimethyltrideca-3,7,11-trienyl)chroman-6-ylphenylsulfonylcarbamate;
2,7,8-trimethyl-2-((3E,7E)-4,8,12-trimethyltrideca-3,7,11-trienyl)chroman -6-ylphenylsulfonylcarbamate;
2,8-dimethyl-2-((3E,7E)-4,8,12-trimethyltrideca-3,7,11-trienyl)chroman-6-ylphenylsulfonylcarbamate;
(R)-2,5,7,8-tetramethyl-2-((3E,7E)-4,8,12-trimethyl-trideca-3,7,11-trienyl)chroman-6-yl tosylcarbamate;
(R)-2,7,8-trimethyl-2-((3E,7E)-4,8,12-trimethyltrideca-3,7,11-trienyl)chroman-6-yl tosylcarbamate;
(R)-2,8-dimethyl-2-((3E,7E)-4,8,12-trimethyltrideca-3,7,11-trienyl)chroman-6-yl tosylcarbamate;
(R)-2,5,7,8-tetramethyl-2-((3E,7E)-4,8,12-trimethyl-trideca-3,7,11-trienyl)chroman-6-yl 4-chlorophenylsulfonylcarbamate;
(R)-2,7,8-trimethyl-2-((3E,7E)-4,8,12-trimethyltrideca-3,7,11-trienyl)chroman-6-yl 4-chlorophenylsulfonylcarbamate;
(R)-2,8-dimethyl-2-((3E,7E)-4,8,12-trimethyltrideca-3,7,11-trienyl)chroman-6-yl 4-chlorophenylsulfonylcarbamate;
(R)-2,5,7,8-tetramethyl-2-((3E,7E)-4,8,12-trimethyl-trideca-3,7,11-trienyl)chroman-6-yl phenylcarbamate;
(R)-2,7,8-trimethyl-2-((3E,7E)-4,8,12-trimethyltrideca-3,7,11-trienyl)chroman-6-yl phenylcarbamate;
(R)-2,8-dimethyl-2-((3E,7E)-4,8,12-trimethyltrideca-3,7,11-trienyl)chroman-6-yl phenylcarbamate;
(R)-2,5,7,8-tetramethyl-2-((3E,7E)-4,8,12-trimethyl-trideca-3,7,11-trienyl)chroman-6-yl benzylcarbamate;
(R)-2,7,8-trimethyl-2-((3E,7E)-4,8,12-trimethyltrideca-3,7,11-trienyl)chroman-6-yl benzylcarbamate;
(R)-2,8-dimethyl-2-((3E,7E) 4,8,12-trimethyltrideca-3,7,11-trienyl)chroman-6-yl benzylcarbamate;
(R)-2,5,7,8-tetramethyl-2-((3E,7E)-4,8,12-trimethyl-trideca-3,7,11-trienyl)chroman-6-yl benzoylcarbamate;
(R)-2,7,8-trimethyl-2-((3E,7E)-4,8,12-trimethyltrideca-3,7,11-trienyl)chroman-6-ylbenzoylcarbamate; and
(R)-2,8-dimethyl-2-((3E,7E)-4,8,12-trimethyltrideca-3,7,11-trienyl)chroman-6-yl benzoylcarbamate.

118. The composition of matter of claim 20 wherein the functional group contains at least one individual aromatic ring and the center of the individual aromatic ring from the functional group that is closest to the oxygen adjacent the ring structure associated with chromanol is positioned between about 3 angstroms and about 6 angstroms from the oxygen adjacent the ring structure associated with chromanol.

119. The composition of matter of claim 20 wherein the functional group contains at least one individual aromatic ring and the center of the individual aromatic ring from the functional group that is closest to the oxygen adjacent the ring structure associated with chromanol is positioned between about 4.5 angstroms and about 4.6 angstroms from the oxygen adjacent the ring structure associated with chromanol.

120. A composition of matter comprising a compound having the general formula:

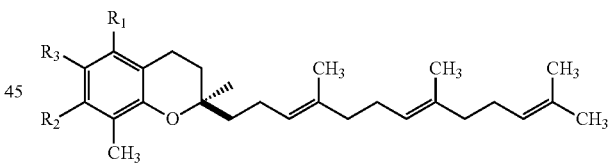

wherein $R_1$ is either H or $CH_3$;
wherein $R_2$ is either H or $CH_3$; and
wherein $R_3$ is a carbamate.

* * * * *